US009687848B2

United States Patent
Makarewicz, Jr. et al.

(10) Patent No.: US 9,687,848 B2
(45) Date of Patent: Jun. 27, 2017

(54) MICROFLUIDIC SYSTEM WITH FLUID PICKUPS

(71) Applicant: Bio-Rad Laboratories, Inc., Hercules, CA (US)

(72) Inventors: Anthony J. Makarewicz, Jr., Livermore, CA (US); Luc Bousse, Los Altos, CA (US); Stefano Schiaffino, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/230,757

(22) Filed: Aug. 8, 2016

(65) Prior Publication Data
US 2016/0339436 A1 Nov. 24, 2016

Related U.S. Application Data

(62) Division of application No. 14/312,488, filed on Jun. 23, 2014, now Pat. No. 9,409,174.

(60) Provisional application No. 61/838,063, filed on Jun. 21, 2013.

(51) Int. Cl.
*B01L 3/00* (2006.01)
*C12N 15/10* (2006.01)
*B01L 7/00* (2006.01)

(52) U.S. Cl.
CPC ..... *B01L 3/502784* (2013.01); *B01L 3/50273* (2013.01); *B01L 3/502715* (2013.01);
(Continued)

(58) Field of Classification Search
CPC ........ B01J 19/0046; B01J 2219/00585; G01N 2021/7763
(Continued)

(56) References Cited

U.S. PATENT DOCUMENTS

| 6,046,056 A | 4/2000 | Parce et al. |
| 8,394,324 B2 | 3/2013 | Bousse et al. |
| 2001/0048899 A1* | 12/2001 | Marouiss ............ B01L 3/50853 422/505 |

(Continued)

FOREIGN PATENT DOCUMENTS

| EP | 2436445 A2 | 4/2012 |
| WO | 02072423 A1 | 9/2002 |
| WO | 2011002957 A2 | 1/2011 |

OTHER PUBLICATIONS

European Patent Office, "Extended European Search Report" in connection with related European Patent App. No. 14812997.6, dated Dec. 21, 2016, 8 pages.
Young, Lee W., Authorized Officer, U.S. Receiving Office, "International Search Report" in connection with related International Application No. PCT/US2014/043715, dated Jan. 14, 2015, 5 pages.
Young, Lee W., Authorized Officer, U.S. Receiving Office, "Written Opinion of the International Searching Authority" in connection with related International Application No. PCT/US2014/043715, dated Jan. 14, 2015, 8 pages.

*Primary Examiner* — Natalia Levkovich
(74) *Attorney, Agent, or Firm* — Kolisch Hartwell, P.C.

(57) ABSTRACT

Microfluidic system, including methods and apparatus, for processing fluid, such as by droplet generation. In an exemplary method, a sample-containing fluid may be dispensed into a well through a sample port of a channel component. The channel component may include (a) a body having a bottom surface attached to the well, and a top surface with a microchannel formed therein, and (b) an input tube projecting into the well from the bottom surface of the body. The sample-containing fluid when dispensed may contact a bottom end of the input tube and may be retained, with assistance from gravity, out of contact with the microchannel. A pressure differential may be created that drives at least a portion of the sample-containing fluid from the well via the input tube and through the microchannel.

17 Claims, 12 Drawing Sheets

(52) U.S. Cl.
CPC ...... *C12N 15/1075* (2013.01); *B01L 3/50853* (2013.01); *B01L 7/52* (2013.01); *B01L 2200/027* (2013.01); *B01L 2300/04* (2013.01); *B01L 2300/044* (2013.01); *B01L 2300/046* (2013.01); *B01L 2300/0672* (2013.01); *B01L 2300/0829* (2013.01); *B01L 2300/0861* (2013.01); *B01L 2400/049* (2013.01); *B01L 2400/0457* (2013.01); *B01L 2400/0487* (2013.01); *B01L 2400/0655* (2013.01); *B01L 2400/0677* (2013.01); *Y10T 436/2575* (2015.01)

(58) Field of Classification Search
USPC .................................................. 436/180, 174
See application file for complete search history.

(56) References Cited

U.S. PATENT DOCUMENTS

| | | |
|---|---|---|
| 2002/0187557 A1 | 12/2002 | Hobbs et al. |
| 2003/0215957 A1 | 11/2003 | Lemmo et al. |
| 2005/0130318 A1 | 6/2005 | Vann et al. |
| 2010/0224255 A1 | 9/2010 | Mathies et al. |
| 2010/0234674 A1 | 9/2010 | Wheeler et al. |
| 2012/0180884 A1 | 7/2012 | Brunello et al. |
| 2012/0190032 A1 | 7/2012 | Ness et al. |
| 2012/0241015 A1 | 9/2012 | Hansen et al. |
| 2012/0261013 A1 | 10/2012 | Gilbert et al. |
| 2013/0090268 A1 | 4/2013 | Hung et al. |
| 2013/0105319 A1 | 5/2013 | Bhattacharya et al. |

\* cited by examiner

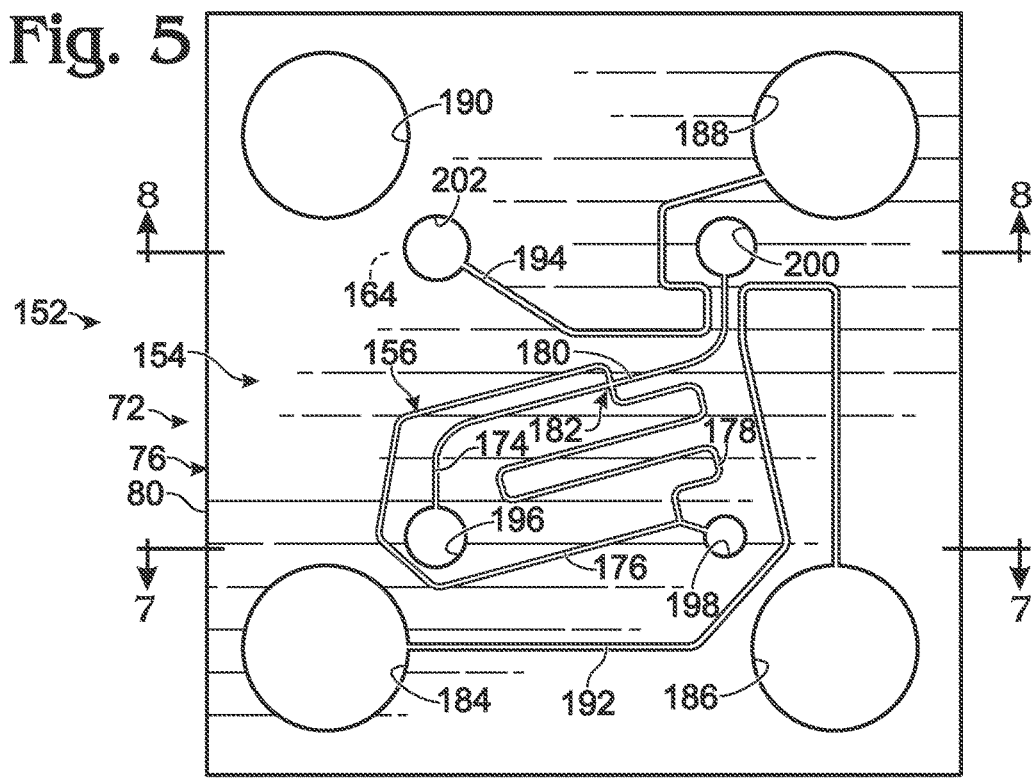
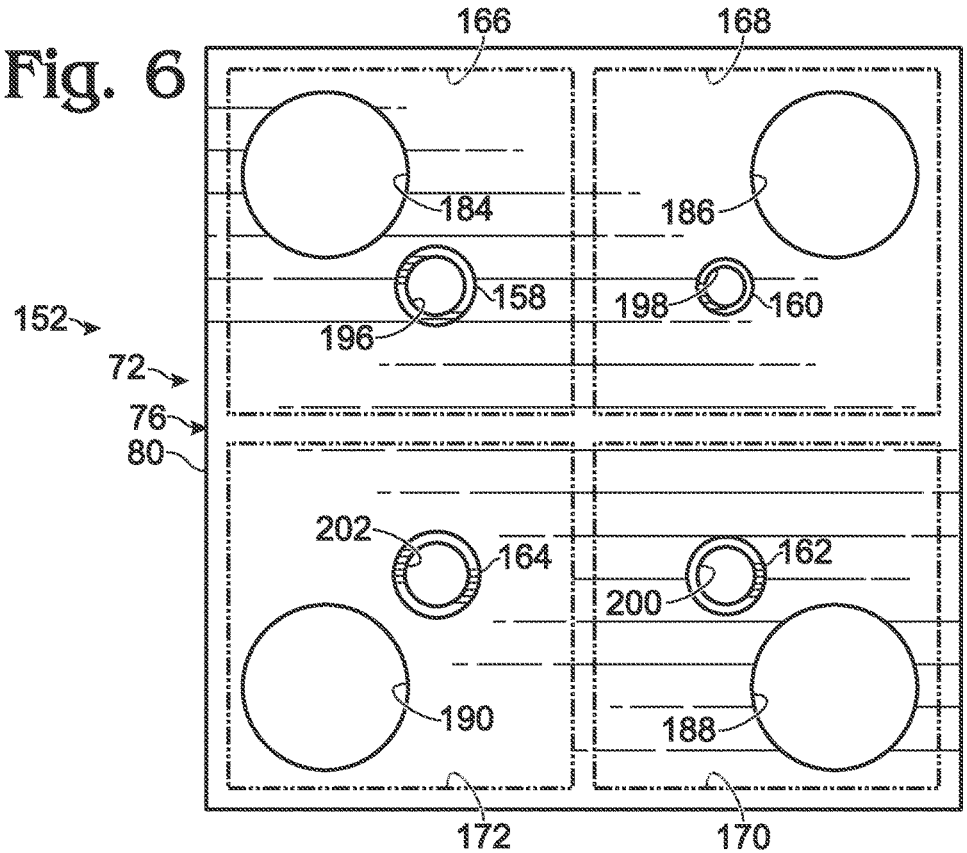

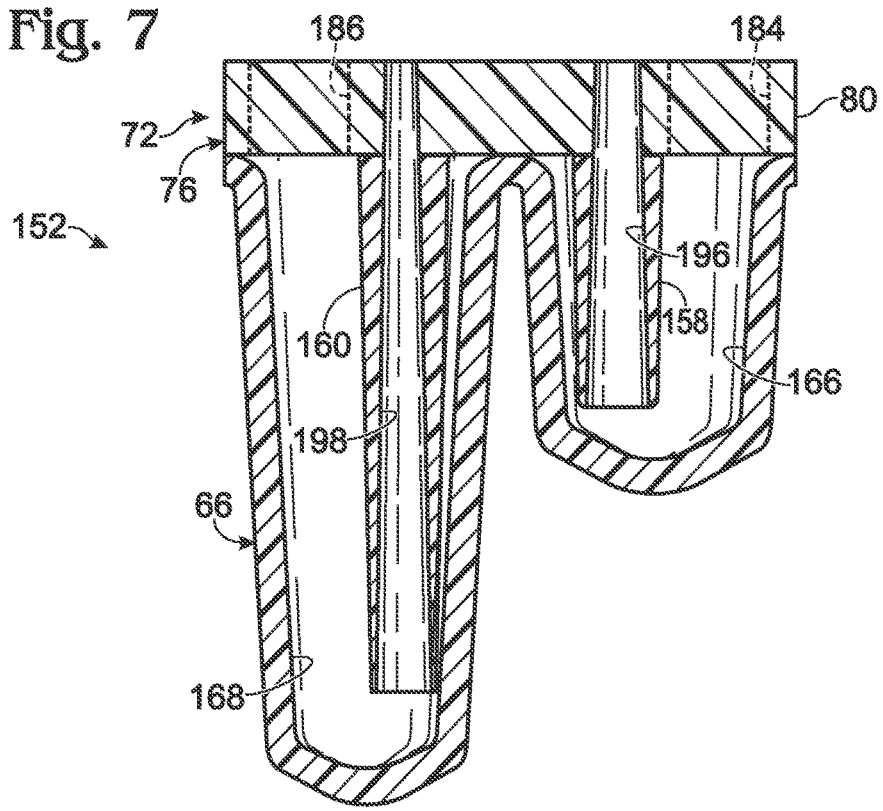
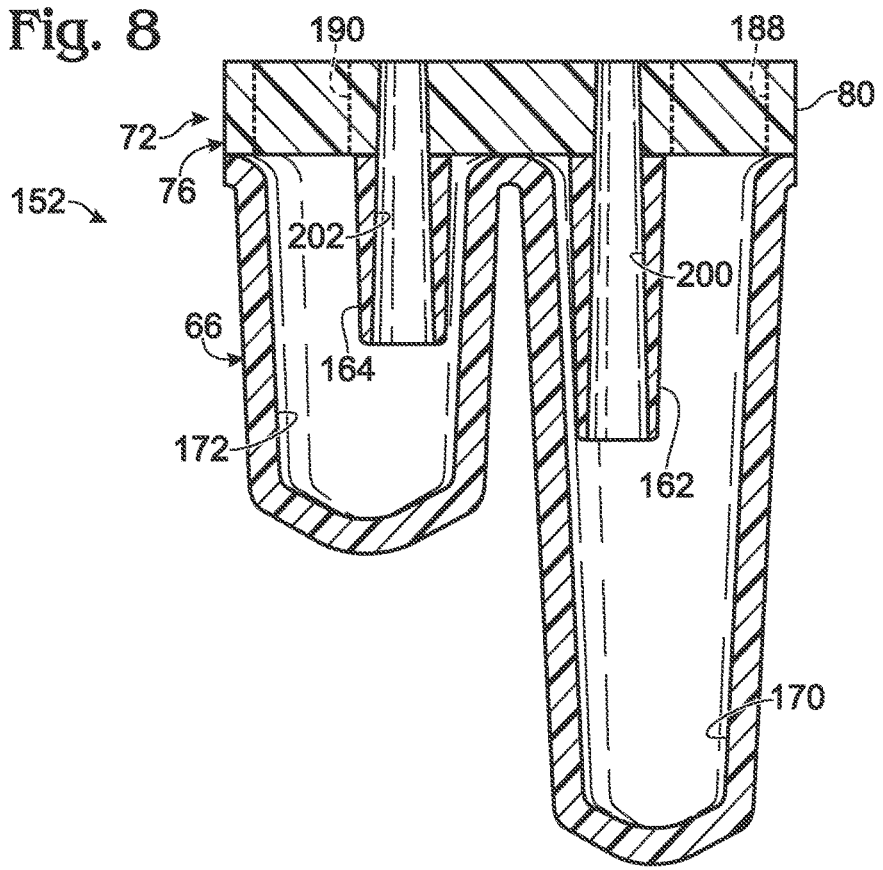

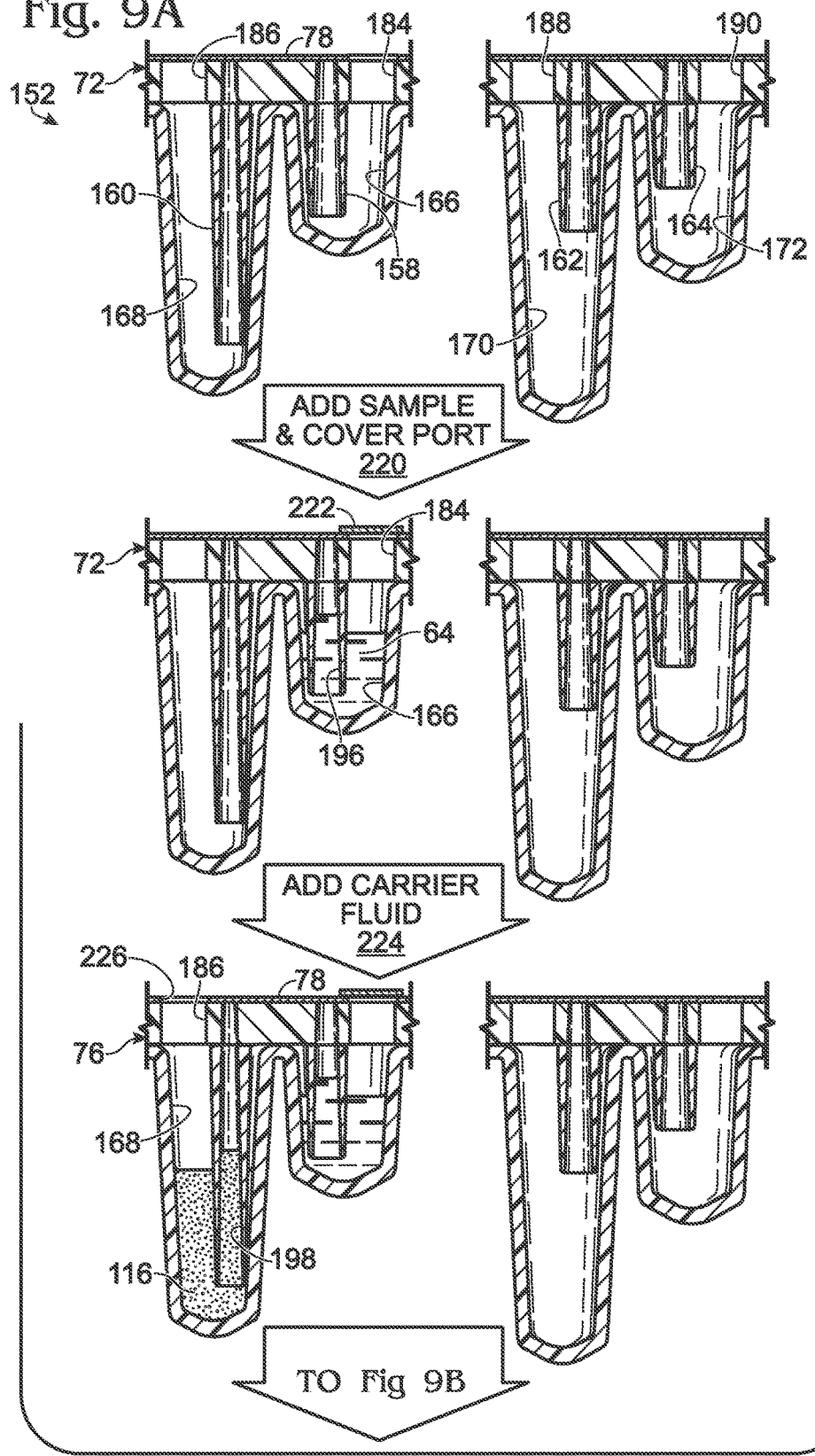

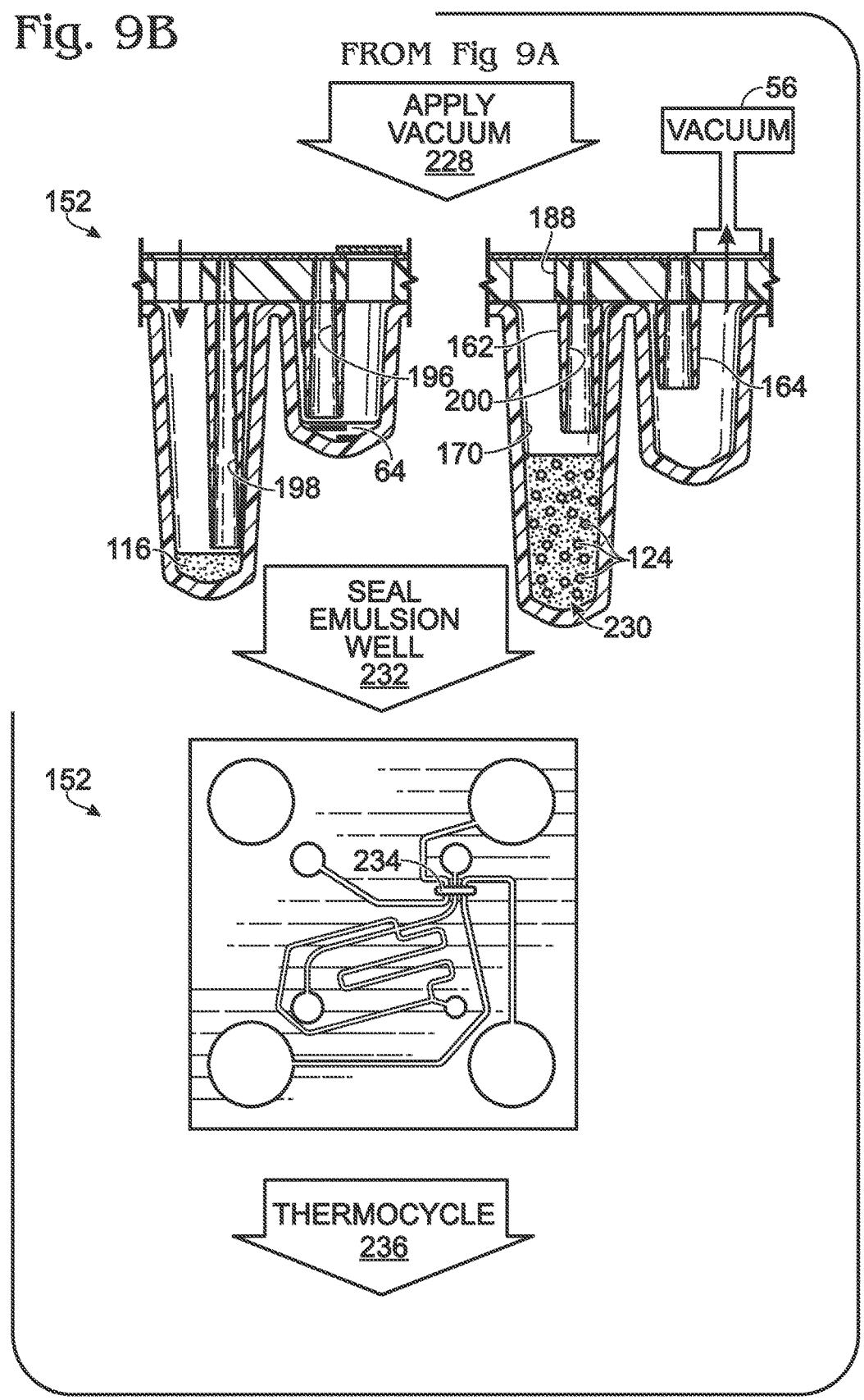

MICROFLUIDIC SYSTEM WITH FLUID PICKUPS

CROSS-REFERENCES TO PRIORITY APPLICATIONS

This application is a divisional of U.S. patent application Ser. No. 14/312,488, filed Jun. 23, 2014, issued Aug. 9, 2016, as U.S. Pat. No. 9,409,174. The '488 application, in turn, is based upon and claims the benefit under 35 U.S.C. §119(e) of U.S. Provisional Patent Application Ser. No. 61/838,063, filed Jun. 21, 2013. Each of these priority applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217711 A1, published Sep. 8, 2011; U.S. Patent Application Publication No. 2012/0152369 A1, published Jun. 21, 2012; U.S. Patent Application Publication No. 2012/0190032 A1, published Jul. 26, 2012; U.S. Patent Application Publication No. 2014/0024023 A1, published Jan. 23, 2014; and Joseph R. Lakowicz, PRINCIPLES OF FLUORESCENCE SPECTROSCOPY ($2^{nd}$ Ed. 1999).

INTRODUCTION

Many biomedical applications rely on high-throughput assays of samples combined with reagents. For example, in research and clinical applications, high-throughput genetic tests using target-specific reagents can provide high-quality information about samples for drug discovery, biomarker discovery, and clinical diagnostics, among others. As another example, infectious disease detection often requires screening a sample for multiple genetic targets to generate high-confidence results.

The trend is toward reduced volumes and detection of more targets. However, creating and mixing smaller volumes can require more complex instrumentation, which increases cost. Accordingly, improved technology is needed to permit testing greater numbers of samples and combinations of samples and reagents, at a higher speed, a lower cost, and/or with reduced instrument complexity.

Emulsions hold substantial promise for revolutionizing high-throughput assays. Emulsification techniques can create millions of aqueous droplets that function as independent reaction chambers for biochemical reactions. For example, an aqueous sample (e.g., 200 microliters) can be partitioned into droplets (e.g., four million droplets of 50 picoliters each) to allow individual sub-components (e.g., cells, nucleic acids, proteins) to be manipulated, processed, and studied discretely in a massively high-throughput manner.

Splitting a sample into droplets offers numerous advantages. Small reaction volumes (e.g., picoliters to nanoliters) can be utilized, allowing earlier detection by increasing reaction rates and forming more concentrated products. Also, a much greater number of independent measurements (e.g., thousands to millions) can be made on the sample, when compared to conventional bulk volume reactions performed on a microliter scale. Thus, the sample can be analyzed more accurately (i.e., more repetitions of the same test) and in greater depth (i.e., a greater number of different tests). In addition, small reaction volumes use less reagent, thereby lowering the cost per test of consumables. Furthermore, microfluidic technology can provide control over processes used for the generation, mixing, incubation, splitting, sorting, and detection of droplets, to attain repeatable droplet-based measurements.

Aqueous droplets can be suspended in oil to create a water-in-oil emulsion (W/O). The emulsion can be stabilized with a surfactant to reduce or prevent coalescence of droplets during heating, cooling, and transport, thereby enabling thermal cycling to be performed. Accordingly, emulsions have been used to perform single-copy amplification of nucleic acid target sequences in droplets using the polymerase chain reaction (PCR).

Compartmentalization of single copies of a nucleic acid target in droplets of an emulsion alleviates problems encountered in amplification of larger sample volumes. In particular, droplets can promote more efficient and uniform amplification of targets from samples containing complex heterogeneous nucleic acid populations, because sample complexity in each droplet is reduced. The impact of factors that lead to biasing in bulk amplification, such as amplification efficiency, G+C content, and amplicon annealing, can be minimized by droplet compartmentalization. Unbiased amplification can be critical in detection of rare species, such as pathogens or cancer cells, the presence of which could be masked by a high concentration of background species in complex clinical samples.

Despite their allure, emulsion-based assays present technical challenges for high-throughput testing, which can require creation of tens, hundreds, thousands, or even millions of individual samples and sample/reagent combinations. Droplet generation, in particular, poses a special challenge. Current droplet generators require mechanisms for holding sample back from the point of droplet generation until a proper pressure environment is established and oil is introduced to the droplet generation point. In the past, this has been done primarily by introducing air traps in the sample line, which can require several minutes of delay in wicking of the aqueous sample. It also has been done by introducing valves into the microfluidic lines, which complicates both fabrication and ease of operation. Moreover, current droplet generators bubble air through the generated droplets after sample processing has been completed, a phenomenon that is known to damage droplets. Thus, there is a need for improved approaches for the generation of droplets.

SUMMARY

The present disclosure provides a microfluidic system, including methods and apparatus, for processing fluid, such as by droplet generation. In some embodiments, the system may include a well and a channel component attached to the well. The channel component may include (a) a body, (b) an input tube (a "fluid pickup") projecting from a bottom surface of the body and having an open bottom end disposed in the input well, (c) a microchannel, and (d) a passage extending through the input tube and the body and connecting the well to the microchannel. The system may be configured to receive a sample-containing fluid in the well and retain the sample-containing fluid below a top end of the passage, until a pressure differential is created that drives at least a portion of the sample-containing fluid from the well via the passage and through the microchannel.

BRIEF DESCRIPTION OF THE DRAWINGS

FIG. 5 is a fragmentary plan view of the base of the channel component of the device of FIG. 3, taken around the single emulsion production unit of FIG. 4.

FIG. 6 is a fragmentary bottom view of the base of the channel component of the device of FIG. 3, taken as FIG. 5 except from the opposite direction.

FIG. 7 is a fragmentary sectional view of the base and the well component of the device of FIG. 3, taken generally along line 7-7 of FIG. 5 through a single emulsion production unit.

FIG. 8 is another fragmentary sectional view of the base and the well component of the device of FIG. 3, taken generally along line 8-8 of FIG. 5 through a single emulsion production unit.

FIG. 9, presented as FIGS. 9A and 9B on separate pages, is a flowchart illustrating exemplary steps that may be performed in a method of generating droplets with the device of FIG. 3, with fragmentary portions of the device shown in cross section before and after performance of each step, in accordance with aspects of the present disclosure.

DETAILED DESCRIPTION

Figure 1:
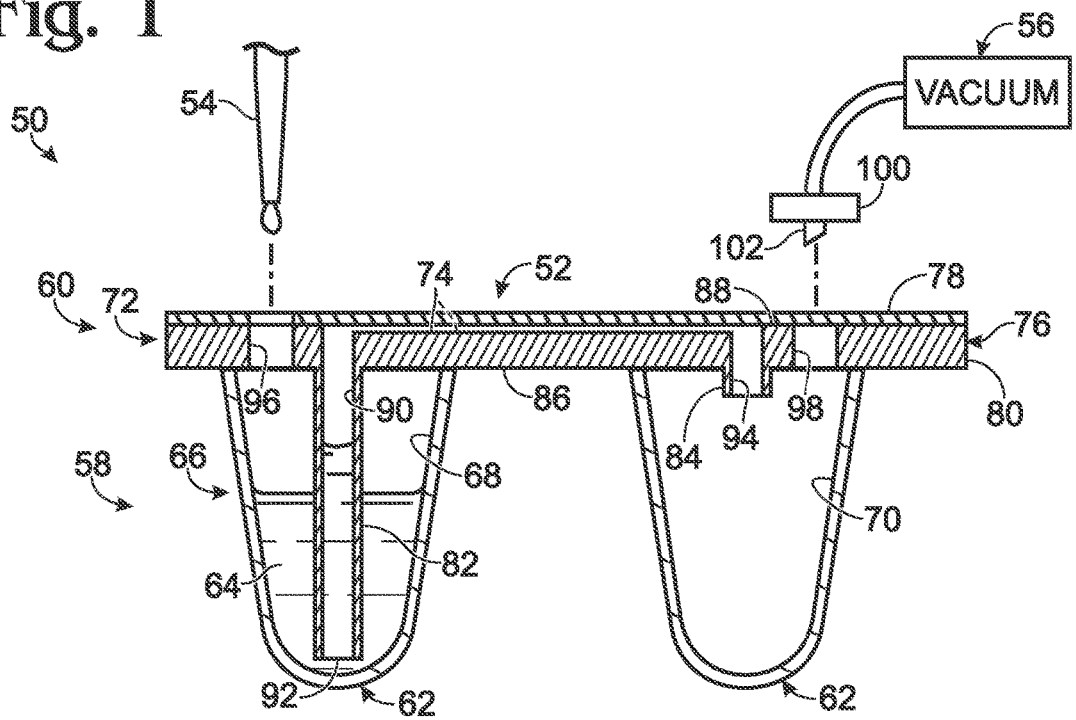
FIG. 1 is a schematic sectional view of selected aspects of an exemplary microfluidic system for fluid processing and including a microfluidic device having an input tube projecting into an input well, with the input tube in contact with a fluid sample contained by the input well and in communication with a microchannel disposed above the input well, and with the fluid sample retained in the well with the assistance of gravity, in accordance with aspects of the present disclosure.

The present disclosure provides a microfluidic system, including methods and apparatus, for processing fluid, such as by droplet generation. In some embodiments, the system may include a well and a channel component attached to the well. The channel component may include (a) a body, (b) an input tube (a "fluid pickup") projecting from a bottom surface of the body and having an open bottom end disposed in the input well, (c) a microchannel, and (d) a passage extending through the input tube and the body and connecting the well to the microchannel. The system may be configured to receive a sample-containing fluid in the well and retain the sample-containing fluid below a top end of the passage, until a pressure differential is created that drives at least a portion of the sample-containing fluid from the well via the passage and through the microchannel.

The present disclosure provides systems, including methods and apparatus, for generating droplets suitable for droplet-based assays. The systems may include (A) a channel component (e.g., a droplet generation component) for forming droplets, (B) a well component for holding sample before droplet generation and for holding generated sample-containing droplets after droplet generation, and (C) an input tube (and, optionally, an output tube) operatively disposed between the channel component and the well component, for introducing sample into the channel component before droplet generation (and, optionally, for depositing generated droplets back into a respective well(s) of the well component after droplet generation, in optional anticipation of further processing and/or analysis). The flow of fluid into, within, and out of the system may be controlled by creation of a pressure differential, for example, by application of a suitable vacuum.

The system may comprise a single-piece device (i.e., the device may be integral or monolithic) or a device formed by two or more pieces (e.g., the device may be modular). In the latter case, components of the device may be joined via any suitable mechanism, such as snapping or adhering, to form the complete device. The channel component may be positioned above and/or over the well component in use, with pickup tubes disposed in between. A sample-containing fluid (interchangeably termed a "sample," a "sample fluid," or a "fluid sample"), a carrier fluid, and an emulsion may then be held in respective wells at least partially by gravity. In addition, sample-containing fluid (and, optionally, carrier fluid) may then be drawn up against gravity from a sample well (and, optionally, a carrier fluid well) through one or more input tube(s), processed to form droplets in the channel component, and then deposited back down into an emulsion well(s) through output tubes, in the direction of, and with the possible assistance of, gravity. The system may be wholly or partially disposable (particularly portions of the system that contact sample and that would thus subject subsequent samples to contamination).

The channel component configured as a droplet generation component may include any suitable mechanism(s) for forming droplets. Typically, this will involve forming sample-containing droplets by merging an aqueous, sample-containing fluid with a carrier fluid, such as oil, to form an emulsion of sample-containing aqueous droplets suspended in the carrier fluid. Channels may be provided to transport the sample-containing fluid and carrier fluid and the sample-containing droplets within the droplet generation component. In some embodiments, the droplet generation component may be at least substantially planar, with droplets generated within a substantially planar channel network disposed in a droplet generation "chip component."

The well component may comprise any suitable collection of reservoirs for holding the respective fluids and droplets. Wells for sample and emulsion, and, optionally, carrier fluid and/or vacuum access, may independently be of any suitable size and shape. Wells in a given embodiment may be of the same or different sizes and/or shapes, relative to one another. For example, among other possibilities, wells for carrier fluid and emulsion may be largest and deepest, the well for sample may be smallest and shallowest, and the well for vacuum access may be of intermediate size and depth.

The input and output (or pickup and deposit (or delivery (or deposit)) tubes may comprise any suitable fluidic connection between the droplet generation component and the well component consistent with the pickup and deposit functions described above. In particular, they may form hollow fluidic connections between channels in the droplet generation component and fluid wells in the well component, acting as fluid pickups or "sippers" to obtain fluid from certain wells and/or to deliver fluid to other wells through the channels. The tubes, like the wells, may independently be of any suitable size (length and internal and external diameter) and shape. Moreover, in a given embodiment, the tubes may be the same or different sizes and shapes, relative to one another. The sample tube and, optionally, carrier fluid tube may be configured (e.g., sized lengthwise) to maintain continuous contact with sample and carrier fluid, respectively, while the system is in use. The droplet or emulsion tube, in contrast, may be configured to avoid contact with droplets once they are deposited in the emulsion well (e.g., by allowing emulsion to separate from the droplet tube and drip or fall into the emulsion well). Thus, if the carrier fluid and emulsion wells are of the same or comparable size, the carrier fluid tube may be longer, and the emulsion well tube may be shorter, relative to one another. The tubes may have internal diameters sufficient to reduce or prevent capillary movement of sample and carrier fluid to the channel network of the droplet generation component. These internal diameters may vary, depending on the fluid and on the composition of the (fluid-contacting portion of the) tube. The various tubes and the droplet generation component may be formed as one piece or from separate pieces that are joined together.

The system may be preconfigured in different formats, depending on intended use, intended user, and so on. For example, the system may be pre-loaded with carrier fluid, so that the user only needs to add sample and a vacuum (or pressure) source. The system may include a pierceable cover, which may be pierced just prior to or simultaneous with the introduction of sample, to reduce contamination. The system also may be replicated, for example, on a microplate footprint, to allow simultaneous processing of multiple samples and/or multiple replicates of a single sample.

The system may provide significant advantages over current systems. For example, the input tube for a sample may be configured to allow gravity to limit the filling of the channel component with the sample, overcoming capillary action, and reducing or avoiding the need for air traps and/or valves by holding the sample away from the channel component. Alternatively, or in addition, the output tube(s), for outputting processed fluid (e.g., an emulsion) from the channel component may allow the processed fluid to drip into a receiving well, reducing or preventing bubbling of air through processed fluid. Additional features of the system may ease workflow. First, open channels in the channel component may be fed through a central location so that they can be resealed after fluid processing (e.g., droplet generation) through a melting process, termed "heat staking." Second, wells of the well component may be fluidically connected, for example, via a microchannel, to enable venting of both wells with a single puncture of a penetrable cover of the channel component. Third, the vacuum tube, or dripper, if present, may reduce the likelihood that the vacuum interface will be contaminated, even if there is an overflow.

Droplet generation systems according to the present disclosure may be part of an overall assay system configured to test for the presence of a target (e.g., a target molecule or target sequence) in a sample. These overall systems may include methods and apparatus for (A) preparing a sample, such as a clinical or environmental sample, for analysis, (B) separating copies of the target by partitioning the sample into droplets each containing no copies or one or more copies of the target (such as a single copy of a nucleic acid target or other analyte of interest), (C) amplifying or otherwise reacting the target within the droplets, (D) detecting the amplified or reacted target, or characteristics thereof, and/or (E) analyzing the resulting data. In this way, complex samples may be converted into a plurality of simpler, more easily analyzed samples, with concomitant reductions in background and assay times. Exemplary systems (including exemplary droplet generators) are described in the patent documents listed above under Cross-References and incorporated herein by reference.

Additional features of fluid processing systems according to the present disclosure, as well as exemplary embodiments, are described in the following sections: (I) overview of microfluidic systems for fluid processing, and (II) examples.

I. OVERVIEW OF MICROFLUIDIC SYSTEMS FOR FLUID PROCESSING

Figure 2:
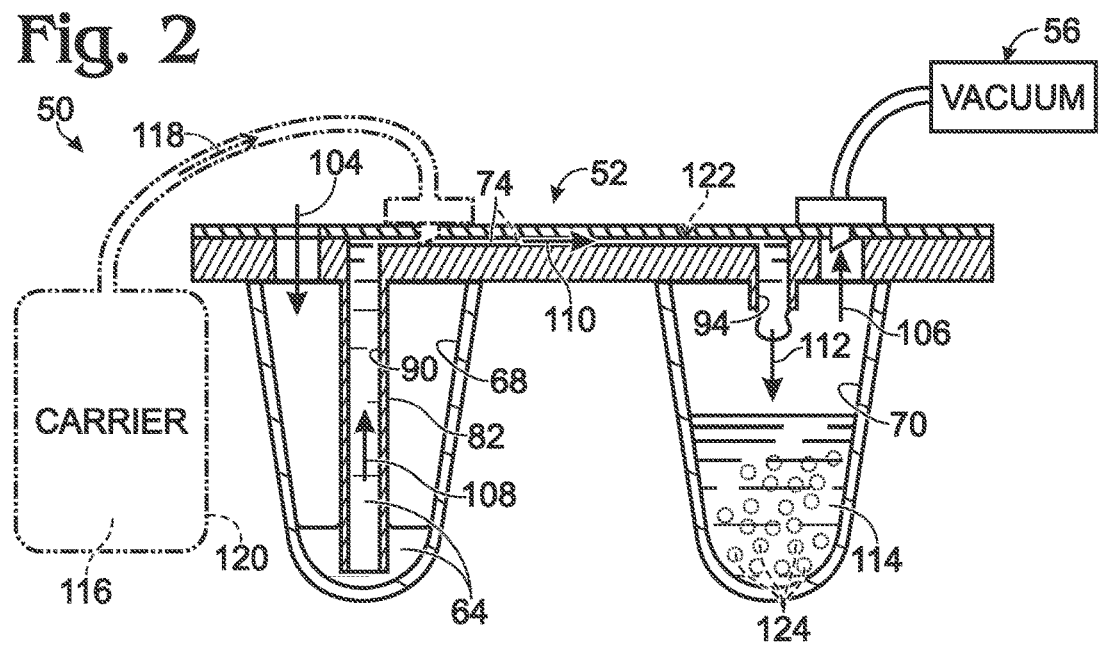
FIG. 2 is another schematic sectional view of selected aspects of the microfluidic system of FIG. 1, taken after a pressure differential has been created by application of a vacuum to the microfluidic device, to drive the fluid sample from the input well to an output well via the input tube and the microchannel, in accordance with aspects of the present disclosure.

This section provides an overview of microfluidic systems for processing fluid and including an input well and a microchannel in fluid communication with the input well via an input tube extending into the input well; see FIGS. 1 and 2.

FIG. 1 shows selected aspects of an exemplary microfluidic system 50 for fluid processing. The system may include a microfluidic device 52 to hold fluid and direct fluid flow, a fluid-transfer device 54 to introduce fluid into and/or remove fluid from device 52, and at least one vacuum/pressure source 56, which may include at least one pump, to drive fluid flow within the device.

Device 52 may include a fluid-holding portion 58 that is attached or attachable to a fluid-processing portion 60. The fluid-processing portion, and particularly a microfluidic region thereof, may be disposed above, and optionally over, the fluid-processing portion.

Fluid-holding portion 58 may include one or more reservoirs 62 to hold one or more fluids such as at least one sample-containing fluid 64, a carrier fluid (interchangeably termed a carrier), an emulsion including sample-containing droplets (interchangeably termed sample droplets) disposed in the carrier, or any combination thereof, among others. Each fluid may include or be liquid and may be held in the fluid-holding portion for a variable/desirable time before and/or after the fluid is introduced into and/or received from the fluid-processing portion.

The fluid-holding portion may include at least one well component 66 that provides at least one well. For example, well component 66 may provide at least one input well 68 to hold fluid for introduction into fluid-processing portion 60 and at least one output well 70 to collect and hold fluid received from one or more input wells via the fluid-processing portion. In some embodiments, the input well and the output well may be formed by discrete well components, and the output well may not be attached to the fluid-processing portion and/or may be removable from the fluid-processing portion. For example, the output well may be provided by a receptacle, such as a tube, that is removable from the fluid-processing portion for further processing, such as thermocycling to promote nucleic acid amplification. In some embodiments, well component 66 may be molded, such as injection molded, as a single piece. The well component may be formed of polymer, such as plastic.

Fluid-processing portion 60 may include a channel component 72 that includes one or more channels 74. In some embodiments, the channel component may be described as a droplet generation component. Each channel 74 may be enclosed, at least between its ends, by channel component 72. At least one channel 74 may be a "microchannel" (also termed a "microfluidic channel"), namely, any channel having a characteristic transverse dimension (e.g., a diameter) of less than one millimeter. A "microfluidic device" and a "microfluidic system" each have at least one microchannel.

Each channel, whether or not microfluidic, can be circumferentially bounded between its ends (i.e., a bounded channel), or may be open on one side (e.g., a groove that is bounded below and on both lateral sides but open above (i.e., an unbounded or uncapped channel)). The same channel may be described as having a conceptually (or literally) unbounded form (e.g., a groove formed in a base (or cap) of the channel component) and a bounded form (e.g., the groove covered by a cap (or base) attached to the base (or cap)).

In some embodiments, the channel component may include a plurality of fluidically connected channels forming a channel network. The channel network may provide a channel intersection at which two or more channels meet to provide a droplet generator (interchangeably termed a site of droplet generation). The channel network and/or one or more channels 74 may be planar. The channel network and/or one or more channels 74, such as one or more microchannels, may be horizontal.

Channel component 72 may be formed integrally as a single piece, or may be composed of two or more pieces that are formed separately and then attached to one another. For example, channel component 72 may include a lower member 76 (interchangeably termed a base) and an upper member 78 (interchangeably termed a cap or cover). Base 76 may include a body 80 and one or more tubes, such as at least one input tube 82 and/or at least one output tube 84. In some embodiments, base 76 may be molded, such as injection molded, as a single piece. The base may be formed of polymer, such as plastic.

Each tube may be attached to body 80. The tube may be formed integrally with the body, or formed separately and then attached to the body. In either case, the tube may be permanently attached to the body and fixed in position with respect to the body. An input tube interchangeably may be described as a straw, a sipper, or a pickup. An output tube interchangeably may be described as a dripper.

The body may have any suitable structure. The body may be described as a substrate, a chip, or a chip component. The body may be planar. A bottom surface 86 of the body may be attached to well component 66, such as to form a fluid-tight seal between the body and one or more wells (and/or each well) of the well component. The body and a well collectively may form a chamber to hold fluid, with body 80 and/or channel component 72 forming a ceiling of the chamber and/or a cover for the well. Body 80 may at least partially bound each channel 74. A top surface 88 of the body may have at least a lower portion of each channel 74 formed therein. For example, a bottom wall and opposing lateral side walls (or lower side wall regions) of channel 74 may be formed in top surface 88. In some embodiments, a bottom surface of the cap alternatively or also may have one or more channels formed therein (see below). The top surface and the bottom surface each may be substantially planar.

Body 80 and input tube 82 collectively may form a passage 90 that fluidically connects the inside of input well 68 to a channel 74. The passage may extend upward from an open bottom end 92 of input tube 82 to the channel, and may be considered as being formed by a hole through input tube 82 that joins an aperture through body 80. Accordingly, the passage may extend through base 76 from a bottom side to a top side of the base. The passage may (or may not) be vertical or at least generally vertical and may be arranged transverse (e.g., substantially orthogonal) to at least one channel 74 and/or a channel network formed by channels 74. Bottom end 92 of input tube 82 may be positioned near the bottom of input well 68, to maximize the uptake of fluid from the input well.

Body 80 and output tube 84 also may define a passage 94 that fluidically connects output well 70 to at least one channel 74. However, in some embodiments, the output tube may extend only into the upper region of the output well (or may be omitted altogether).

Channel component 72 also may define one or more ports, such as an input port 96 and an output port 98. Input port 96 may be formed over the input well and may be contiguous therewith, and provides access to the interior of input well 68 for introduction of sample 64. Accordingly, the input port may be dimensioned to receive a bottom end portion of fluid-transfer device 54, before or as the fluid-transfer device dispenses the sample into the input well. Output port 98 may be structured like the input port and provides access to the interior of output well 70 to allow removal of fluid with another fluid-transfer device 54. The ports shown here are through-holes that extend through body 80 between its top and bottom surfaces. In some embodiments, one or more other ports may be constructed as blind holes in the body that are contiguous with a channel formed in a top surface of the body (e.g., see Example 2).

Cap 78 may be attached to top surface 88 of body 80 in a fluid-tight seal. The cap may be termed a cover, a sealing member, or a capping member, and may be substantially planar. The cap may at least partially bound each channel 74. The cap may form a top wall of each channel, and, in some embodiments, side walls or at least side wall regions of each channel. The cap may be a cover formed as only one layer, or two or more overlapping (or nonoverlapping) layers of material. If the cover is composed of two or more layers, the layers may be connected to the body at the same time or sequentially. For example, the cover may include a first layer attached directly (e.g., bonded) to a top surface of the body and a second layer applied later (e.g., to cover one or more openings defined by the first layer). The cover may (or may not) be substantially thinner than the body, such as less than 20%, 10%, or 5% of the body thickness. In some embodiments, the cover may be thicker than the body.

The cap may cover any suitable openings formed in the top surface of the body. For example, the cap may cover the top end of each passage 90, 94, and may or may not cover each port 96, 98. In some embodiments, the cap may be configured to be pierced at one or more ports during use of the system. Accordingly, any of the ports may be provided as a closed port that can be opened by the user (and/or an instrument) by piercing the cap, which may performed to gain access to an underlying well, and/or to create fluid communication with one or more channels 74. The port may be opened to form a vent and/or a fluid transfer point.

Wells or well protrusions for holding fluid may be formed as one or more well components 66 which are initially separate from body 80 of channel component 72 and which are configured to form a substantially fluid tight seal or interface with the body. In other cases, some or all of the wells may be integrally formed with the body. The well component and the body (and/or channel component) may be configured to mate together. In some cases, the well component and the body (and/or channel component) may be sealed together by a user or during manufacture, to form a substantially fluid tight connection. Furthermore, as described in more detail below, one or both of the well component and the body (and/or channel component) may have a larger format or "footprint" than is depicted in FIG. 1, such as a microplate format, to allow two or more (or many) different samples to be processed (e.g., used to generate droplets) in one system. Components of the system may work together to (A) pick up sample from a sample well, (B) introduce carrier fluid from a carrier reservoir, (C) bring these components together to generate droplets, and (D) dispense the droplets to an emulsion well.

Fluid-transfer device 54 may be any device or set of devices capable of dispensing and/or picking up fluid. Device 54 thus may be a pipette, a syringe, or the like. The device may be operated manually or automatically.

Pressure source 56 may be any device or set of devices capable of creating a pressure differential within device 52. The pressure source 56 may apply (positive) pressure to the device to push fluid, and/or a vacuum (also called suction) to the device to pull fluid. The pressure source may be capable of forming a sealed connection or sealed engagement with device 52, such as via a gasket 100 and/or at least one piercing element 102 that pierces cap 78, among others. The system also or alternatively may include one or more other piercing elements 102 that are operatively positioned or positionable over other ports, such as to vent the system, access or fluidically connect to the ports, or the like. The piercing element may be hollow (e.g., a pointed tube) to permit fluid flow through the pierced cap while the piercing element remains in place.

FIG. 1 shows input tube 82 of base 76 extending into an input well 68 that contains a volume of sample fluid 64. This arrangement allows confinement of the sample fluid by gravity. When a tube is in contact with a fluid (e.g., sample fluid 64) in a reservoir (e.g., well 68), gravity may limit the ability of the fluid to travel up the tube. The capillary rise height H depends on the tube inner radius r, the surface tension γ of the fluid at a liquid-air interface, the density of the fluid ρ, and the contact angle θ of the fluid on the tube surface, according to the following formula:

$$H = \frac{2\gamma \cos\theta}{\rho g r}$$

Provided that the capillary rise height is less than the height difference between the fluid in the well and a channel 74 above the well, gravity will ensure that the fluid cannot reach the channel without application of a driving force, such as a pressure differential. Accordingly, the fluid is retained in the well until the driving force is applied.

In a more specific example, intended only for illustration, assume that channel 74 is located 6 mm above the bottom of the well, and the height of the fluid in the well is 3 mm. The capillary rise for an illustrative sample for PCR may be calculated as approximately 1.3 mm for a 1 mm internal diameter tube. This arrangement positions the sample meniscus inside the tube at 1.7 mm below channel 74.

In some cases, the volume (e.g., the well) into which the tube extends may be closed instead of vented, increasing the retention power of the structures described above. Any capillary rise would be counteracted by an increase of back-pressure in the closed volume, further isolating the fluid in the well from channel 74 above.

FIG. 2 shows system 50 taken after a pressure differential has been created by application of a vacuum to device 52 with pressure source 56. The pressure differential may create pneumatic flow into device 52 (such as flow of air into the input well), indicated by an arrow at 104, and out of device 52 (such as flow of air out of the output well), indicated by an arrow at 106. A pressure difference causes sample fluid 64 to travel up input passage 90, against the force of gravity, indicated by an arrow at 108, from the bottom end of input tube 82. The sample fluid exits input passage 90 and flows through at least one channel 74, indicated by an arrow at 110, and then travels downward, in the direction of gravity, indicated by arrow at 112, through output passage 94 and into output well 70. Outputted fluid 114 is collected in the output well. In the depicted embodiment, air enters device 52 at a position over input well 68 and exits the device at a position over output well 70. In other embodiments, air may enter and/or exit the device at a position that is above but not over the corresponding well, via a horizontally offset vent port or vacuum port.

In some embodiments, the pressure differential drives a carrier fluid 116, indicated by an arrow at 118, from a source of carrier fluid. The source may be within device 52 or may be external to the device (e.g., originating from carrier reservoir 120). The source of carrier fluid may be fluidically connected to one or more channels 74 such that sample fluid 64 and carrier fluid 116 are driven through a channel intersection 122 formed where a plurality of channels 74 meet one another. Sample-containing droplets 124 disposed in carrier fluid 116 (a continuous phase) may be formed at channel intersection 122 and collected in output well 70 (e.g., see Examples 1 and 2).

The channel component may define an open path for fluid flow from the input well to the output well. The path may remain open (unobstructed) as the input well is loaded with sample, while the input well retains the loaded sample with the assistance of gravity, and as the sample is driven to the output well. Accordingly, the channel component and/or the flow path may be described as being valve-less and/or as having valve-less microfluidics.

Figure 2A:
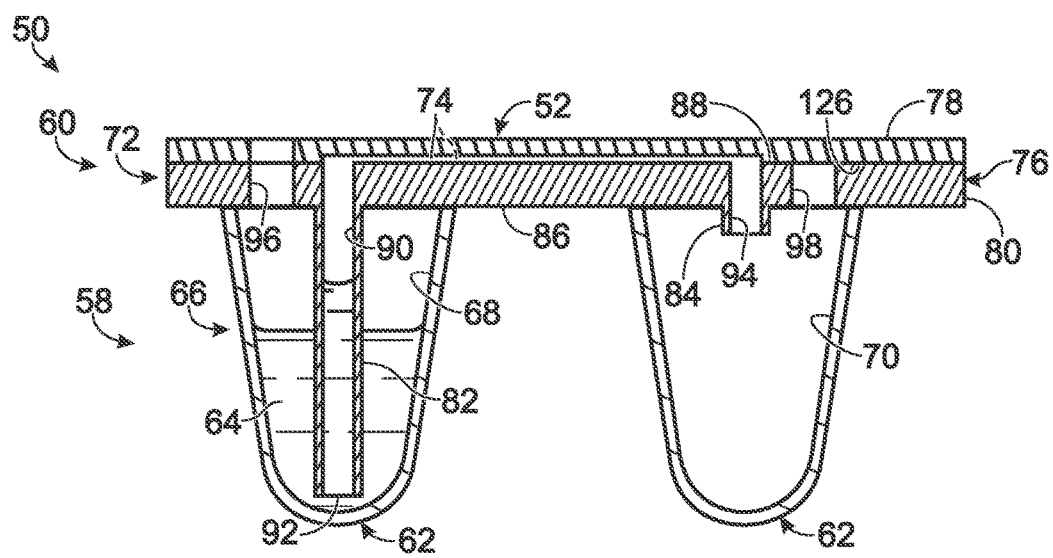
FIG. 2A is a schematic sectional view of selected aspects of a different version of the microfluidic system of FIG. 1, taken as in FIG. 1 and having one or more microchannels formed in a bottom surface of a cap of the channel component, in accordance with aspects of the present disclosure.

FIG. 2A shows a different version of microfluidic system 50 of FIG. 1. The system of FIG. 2A is similar to that of FIG. 1, except that one or more channels 74, such as at least one microchannel and/or a channel network for droplet generation, are formed at least partially in a bottom surface 126 of cap 78 of channel component 72. The bottom surface may be substantially planar. Each channel 74 of device 52 of the system may be formed in bottom surface 126 of cap 78 instead of in a top surface 88 of base 76. The top surface also may be substantially planar. Base 76 may form a bottom wall of each channel 74.

Figure 2B:
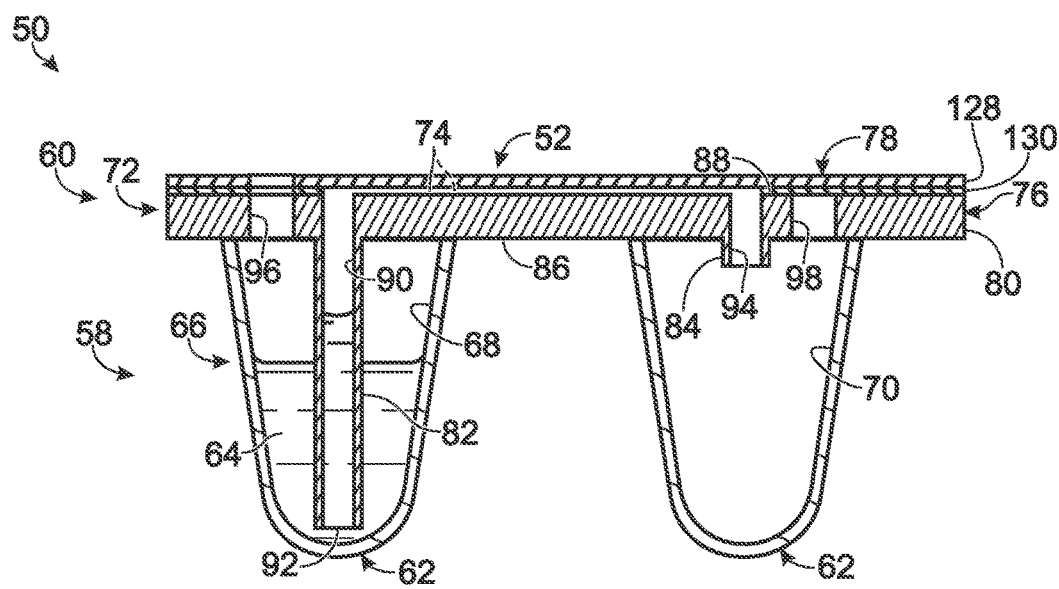
FIG. 2B is a schematic sectional view of selected aspects of another version of the microfluidic system of FIG. 1, taken as in FIG. 1 and having a channel component with a two-layer cap, in accordance with aspects of the present disclosure.

FIG. 2B shows another version of microfluidic system 50 of FIG. 1. The system of FIG. 2B is similar to that of FIG. 2A, except that cap 78 is composed of more than one layer, such as an upper layer 128 (e.g., an upper sheet of material) attached to a lower layer 130 (e.g., a lower sheet of material). Upper layer 128 may be similar or identical to cap 78 of FIG. 1. The upper layer may be substantially planar and/or may have a substantially planar bottom surface forming a top wall of one or more channels 74. Lower layer 130 may be substantially planar and may be sandwiched between upper layer 128 and base 76. The lower layer may form lateral side walls of each channel 74 but neither the top wall nor the bottom wall of each channel. Base 76 may form a bottom wall of each channel 74.

Further aspects of exemplary droplet generation systems that may be suitable for the present fluid processing systems, including microfluidic devices, droplet generators, samples, carrier fluids, droplets, emulsions, droplet-based assays, instruments to drive and control droplet generation, and methods of droplet generation, among others, are described in the patent documents listed above under Cross-References, which are incorporated herein by reference.

II. EXAMPLES

This section describes selected aspects and embodiments of the present disclosure related to systems and methods for fluid processing and/or droplet generation. These examples are intended for illustration only and should not limit or define the entire scope of the present disclosure.

Example 1: Droplet Generation Device with Fluid Pickups for Sample and Carrier This example describes an exemplary embodiment 152 of microfluidic device 52 for fluid processing system 50 (see FIGS. 1, 2, 2A, and 2B) that is configured for generating an array of emulsions, and also describes exemplary methods of using device 152 to generate and process emulsions; see FIGS. 3-9. The emulsions are generated with samples and carrier fluid transported from wells to channels via fixed, dedicated pickup tubes.

Device 152 uses hollow protrusions or "fluid pickups" in conjunction with droplet generators, and provides specific examples of droplet generators in which sample-containing droplets suspended in a carrier fluid are generated and transported substantially within a plane.

As used herein, "substantially within a plane" or "substantially planar" with respect to droplet generation means that the radius of curvature of the space in which droplets are generated and transported is much greater than the cross-sectional dimensions of the channels through which the droplets are created and transported, and the curvature does not substantially alter the hydraulic function of the channels.

Figure 3:
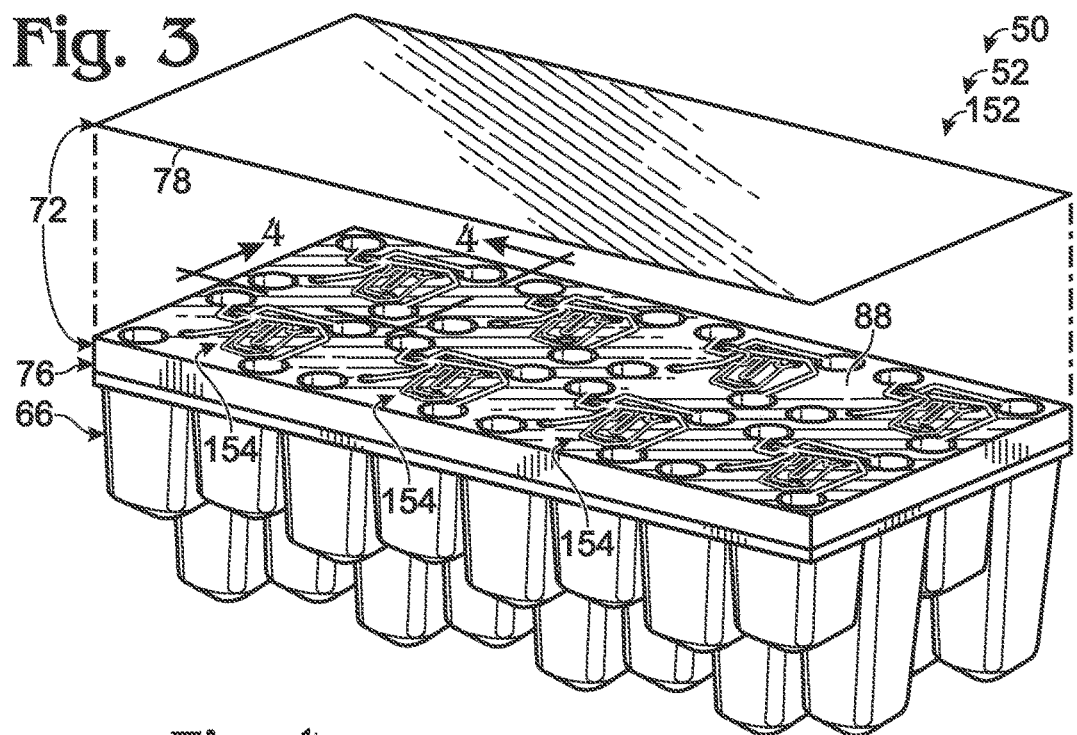
FIG. 3 is a partially exploded view of an exemplary embodiment of the microfluidic device of FIG. 1 constructed as a droplet generation device having an array of emulsion production units and including a channel component attached to and overlying a well component, with the channel component including a base covered by a cap, and with the cap exploded from the base, in accordance with aspects of the present disclosure.

FIG. 3 shows a partially exploded view of device 152. The device has a well component 66 attached to and underlying a channel component 72. The channel component has a base 76 that is attached to wells of well component 66 to form a fluid-tight circumferential seal at the top perimeter of each of the wells. A cap 78 of channel component 72 is shown exploded from base 76, although the cap is typically pre-attached to a top surface 88 of base 76 before use, such as during manufacture of device 152.

Device 152 forms an array of emulsion production units 154. The depicted embodiment has a two-by-four array of units 154, although the device may have any suitable number of the units. The emulsion production units may generate emulsions in parallel, in this case, a set of eight emulsions in parallel. The emulsion production units may be replicates of one another and may be arranged as an SBS-compatible array, such as with a unit repeated every 18, 9, 4.5, 2.25, or 1.125 mm, among others, along each row and column of units 154.

Figure 4:
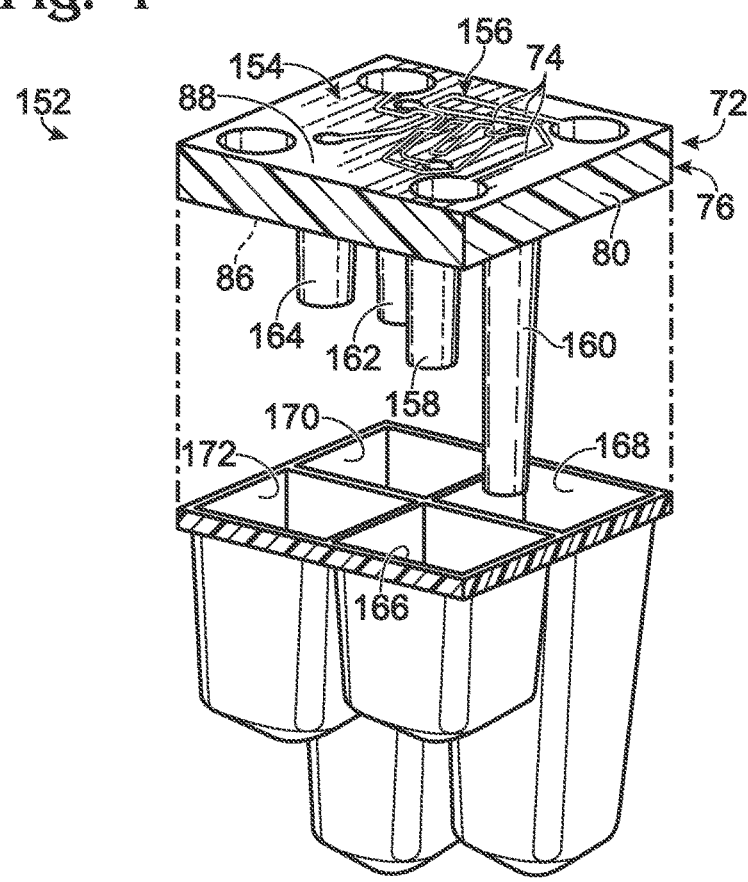
FIG. 4 is an exploded sectional view of the device of FIG. 3, taken generally along lines 4-4 of FIG. 3 in the absence of the cap and showing a single emulsion production unit of the device.

FIG. 4 shows one of emulsion production units 154 in the absence of cap 78. Channel component 72 includes a channel network 156 of channels 74 formed in top surface 88 of a planar body 80 and capped with cap 78 such that each channel is circumferentially bounded along its length. A plurality of tubes project from a bottom surface 86 of the body, namely a sample tube 158, a carrier tube 160, a droplet tube 162, and a vacuum tube 164. Tubes 158 and 160 are input tubes 82, tube 162 is an output tube 84 (see FIGS. 1 and 2), and tube 164 is an optional output-like tube to further separate the vacuum interface from the emulsion. Each of tubes 158, 160, 162, and 164 extends into a respective well of well component 66: tube 158 into a sample well 166 (an input well 68), tube 160 into a carrier well 168 (another input well 68), tube 162 into an emulsion well 170 (an output well 70), and tube 164 into a vacuum well 172. In other embodiments, the channels may be formed in a bottom surface of cap 78 (e.g., see FIGS. 2A and 2B).

FIG. 5 shows channel network 156 in plan view. The network includes a sample channel 174, a plurality of carrier channels 176 and 178, and a droplet channel 180, which intersect at a channel junction 182 (interchangeably termed a droplet generation site) where droplets are generated. (The channels are too small to be visible in the sectional views of FIGS. 6-9.) Sample channel 174 carries sample fluid to junction 182, carrier channels 176 and 178 carry carrier fluid to the junction, and droplet channel 180 carries droplets of the sample fluid in carrier fluid from the junction. In other embodiments, only one carrier channel is present per unit 154.

Base 76 defines a plurality of apertures each extending through the base from a top side to a bottom side of the base (see FIGS. 5-8). Each aperture may extend only through body 80 or through the body and one of tubes 158, 160, 162, or 164.

Ports may be created by apertures that extend only through the body: a sample port 184 (an input port 96), a carrier port 186 (another input port 96), an emulsion port 188 (an output port 98), and a vacuum port 190. A vent channel 192 formed in a top surface of body 80 may connect the sample port and the carrier port, to allow either port to vent the other port. Another channel 194 formed similarly helps to fluidically connect emulsion port 188 with vacuum port 190 via vacuum passage 202.

Sample port 184 is configured to receive a sample, typically in fluid form. For example, sample-containing fluid may be inserted into sample port 184 with a pipette, either manually or as part of an automated system. Sample well 166 of well component 66 is disposed directly under sample port 184, as depicted in FIGS. 6 and 7, so that fluid inserted into the sample port will pass into the sample well.

Carrier port 186 is configured similarly to receive oil or some other carrier fluid. For example, as in the case of the sample-containing fluid, carrier fluid may be inserted into carrier port 186 with a pipette, either manually or as part of an automated system. Carrier well 168 is disposed directly under carrier port 186, as depicted in FIGS. 6 and 7, so that carrier fluid inserted into the carrier port will pass into the carrier well.

Emulsion port 188 is configured to receive an emulsion extractor, such as a needle, pipette, or syringe tip, which can be used to extract the emulsion resulting from the application of vacuum pressure at vacuum port 190. Emulsion well 170 is disposed directly under emulsion port 188, and is configured to receive an emulsion of sample-containing droplets in a manner to be described in more detail below.

Vacuum port 190 (interchangeably termed a vacuum interface) is configured to receive a vacuum connection, such as an end of a vacuum conduit, to apply negative pressure to the vacuum port. As will be described in more detail below, the application of vacuum pressure at vacuum port 190 causes the formation of an emulsion of sample-containing droplets suspended in carrier fluid, and transports the emulsion to emulsion well 170. Vacuum well 172 may be disposed directly under vacuum port 190.

Passages may be created by apertures that extend through the tubes: a sample passage 196 (an input passage 90), a carrier passage 198 (another input passage 90), a droplet passage 200 (an output passage 94), and a vacuum passage 202.

Passages 196, 198, 200, and 202 are each in direct fluid communication with one of the channels of channel network 156, as depicted in FIG. 5. This configuration provides fluid and pressure communication between channel network 156 and the wells of well component 66, as described below.

Sample passage 196 extends through sample tube 158, which also may be referred to as a "sample sipper." When well component 66 and base 76 (and/or channel component 72) are joined together, sample tube 158 is configured to fit within sample well 166, which allows the sample tube later to pick up or "sip" sample-containing fluid from the sample well, and to transport the sample-containing fluid to the top of sample passage 196 and thus to channel network 156. The internal diameter of the sample tube may be large enough to prevent significant capillary movement of sample to a level much above that of the sample in the well outside the tube. As shown in FIG. 7, sample tube 158 extends to a position near the bottom of sample well 166, such that the bottom end of sample passage 196 can pick up at least most of the sample in the well.

Carrier passage 198 extends through carrier tube 160, which also may be referred to as a "carrier sipper." When well component 66 and base 76 (and/or channel component 72) are joined together carrier tube 160 fits within carrier well 168, which allows the carrier tube later to pick up or "sip" carrier fluid from the carrier well, and to transport the carrier fluid to the top of carrier passage 198 and thus to channel network 156. The internal diameter of the carrier tube may be large enough to prevent significant capillary movement of carrier fluid to a level much above that of the carrier fluid in the carrier well outside the tube. As shown in FIG. 7, carrier tube 160 extends to a position near the bottom of carrier well 168, such that the bottom end of carrier tube 160 can pick up at least most of the carrier fluid in the well.

Droplet passage 200 extends through droplet tube 162, which may be referred to as a "droplet dripper." The droplet tube fits within emulsion well 170 and is configured to transport an emulsion of sample-containing droplets suspended in carrier fluid from channel network 156 (and more particularly, droplet channel 180) and into emulsion well 170, from which the emulsion may be extracted as described previously. Transport of the droplets from the channel network into the droplet dripper and then into the emulsion well results from negative pressure applied at vacuum port 190. As shown in FIG. 8, droplet tube 162 does not extend to the lower portion of the emulsion well, to reduce the chance of drawing part of the emulsion to the vacuum well via emulsion port 188, channel 194, and vacuum tube 164.

Vacuum passage 202 extends through vacuum tube 164, which also may be referred to as a "vacuum dripper." The vacuum tube fits within vacuum well 172 and is configured to provide pressure communication between the vacuum well and the emulsion well via channel 194 and emulsion port 188. Vacuum pressure introduced into vacuum port 190 thus may be communicated to sample sipper 158 and carrier sipper 160 through vacuum dripper 164 and channel network 156, causing sample-containing fluid and carrier fluid to be drawn into the channel network through the sample sipper and the carrier sipper, respectively.

A primary cap (such as cap 78) and/or a secondary cap (such as another layer placed on the primary cap) may be placed on and/or over the top surface of body 80, to seal the top of any suitable combination of apertures defined by the body alone or in combination with one or more tubes. For example, the cap may seal channel network 156 or a portion thereof (such as any combination of sample channel 174, carrier channels 176 and 178, and droplet channel 180), one more ports (such as sample port 184, carrier port 186, emulsion port 188, and/or vacuum port 190), and one or more passages (such as sample passage 196, carrier passage 198, droplet passage 200, and/or vacuum passage 202). Each cap may be a substantially planar sheet, optionally treated with an adhesive on the bottom side and optionally having a substantially featureless bottom surface. At least one cap may be applied during manufacture and/or at least one cap may be configured to be applied by a user.

The cap may be pierced by a dedicated instrument or tool, a syringe, and/or a pipette tip, among others. Piercing the cap may create an air intake vent for a port, such as sample port 184 and/or carrier port 186, or an air outflow vent for emulsion port 188 (if pressure is used to drive fluid flow), among others. Alternatively, or in addition, piercing the cap may create an access point for addition of sample to a sample well or carrier fluid to a carrier well, or removal of emulsion from an emulsion well, among others.

In other cases, piercing the cap may create an opening over a vacuum port, such as vacuum port 190. For example, the aperture may be formed by pressing an end of a vacuum conduit through a cover (e.g., only a primary cap, a primary cap and a secondary cap, or both, among others) and into the vacuum port, or by any other suitable method. In any case, the opening may provide an access point for a vacuum source to apply vacuum pressure to the device. As will be described in detail below, this causes formation of an emulsion of sample-containing droplets suspended in carrier fluid, as well as transport of the emulsion through sample sipper 158 and into emulsion well 170.

FIG. 9 shows a flowchart illustrating exemplary steps that may be performed in a method of forming and processing an emulsion with device 152. The device is depicted here in schematic cross section, to place tubes 158 and 160 and ports 184 and 186 in the same plane, and to place tubes 162 and 164 and ports 188 and 190 in the same plane. Sample port 184 may be open on top, as shown, to provide access to sample well 166 from above device 152, or cap 78 may be pierced to provide that access.

Sample 64 may be introduced into device 152, indicated by an arrow at 220. Sample 64 may be dispensed to sample well 166 through sample port 184, and then the port optionally may be covered with a cover element 222. In exemplary embodiments, the cover element is a user-applied adhesive film (e.g., an adhesive tape), which may cover any suitable number of openings in cap 78. The cover element ensures containment of the sample and reduces the chance of cross-contamination with different samples among the emulsion production units. As shown, sample 64 is added to a level that is substantially below the top of the sample well and the top of sample passage 196. Gravity retains the sample in this position, allowing each of the sample wells of the device to be loaded with sample before proceeding with droplet generation.

Carrier fluid 116 may be introduced into device 152, indicated by an arrow at 224. The carrier fluid may be dispensed into carrier well 168 through carrier port 186, before or after the sample is dispensed into the sample well. The device may be supplied to a user with carrier port 186 open at the top (e.g., with an opening 226 defined in cap 78 over the carrier port), or cap 78 may be pierced (manually by the user or automatically with an instrument) to form an opening that opens the carrier port for introduction of carrier fluid through the cap. The carrier fluid, similar to the sample, may be retained in the carrier well by gravity, and below the top of carrier passage 198 inside the passage, until driven out of the carrier well by a pressure differential. Alternatively, the device may be configured such that the carrier fluid can flow to the channel network without a pressure differential. In other embodiments, the carrier fluid may be introduced more directly into the channel network of the device through cap 78 (e.g., from an external reservoir), without passing through base 76 (see Example 2). In other words, carrier well 168 may be omitted from the device.

Vacuum may be applied, indicated by an arrow at 228. The vacuum creates a pressure differential that drives sample 64 and carrier fluid 116 upward through respective passages 196, 198 into the channel network and through a channel intersection thereof to form droplets, and down through droplet passage 200 for collection as an emulsion 230 in emulsion well 170. Application of vacuum may be performed on emulsion production units 154 of device 152 in parallel to form a set of droplets with each unit and collect an emulsion from each unit in parallel.

Each emulsion well may be sealed, indicated at 232. The emulsion well may, for example be sealed by blocking each channel that communicates with the well by applying a heat stake 234 across a portion of the channel network. Heat stake 234 seals (i.e., closes off (blocks)) the channels across which it is disposed, for example, by melting or otherwise deforming the channel walls so that fluid can no longer pass through the channels. Accordingly, heat stake 234 serves to fluidically isolate the emulsion well from the atmosphere and from the rest of the system, such as from the fluid contents of other wells and the rest of the channel network. Similarly, heat stake 234 fluidically isolates the vacuum port, the vacuum well, and the vacuum dripper from the remaining portions of the system. Furthermore, the heat stake partially fluidically isolates the sample port, the sample well, and the sample sipper. The only remaining fluid connection of these sample-related components of the system to other portions of the system is through the channel network to the carrier well.

Fluidic isolation of various components of the system from each other through heat staking, as described above, or by any other means, may be performed after the system is used to generate an emulsion of sample-containing droplets, to insure that the emulsion will remain in the emulsion well, and will not be drawn or otherwise transported back into the channel network. Furthermore, sample-containing fluid will not be able to pass inadvertently to the vacuum port, where it could potentially contaminate the vacuum hose or other fittings, potentially allowing those components to be reused rather than discarded after each use. Another purpose of the fluidic isolation may be to prevent loss of fluid, such as carrier fluid or sample fluid (e.g., water) from the emulsion during thermal cycling, which may expose the emulsion to temperatures sufficient to cause evaporation.

Each emulsion may be thermally cycled (interchangeably termed "thermocycled"), indicated by an arrow at 236. After heat staking or some other form of fluidically isolating the emulsion well, device 152 may be placed in a thermocycler and thermocycled to cause the amplification of any target present in the emulsion within the emulsion well. Finally, an opening may be formed in cap 78 above the emulsion well, over the emulsion port, to open the emulsion port and provide access to the emulsion in the emulsion well. This allows an emulsion extraction tool, such as a pipette, needle, or syringe tip, to be inserted into the emulsion well and to extract the thermocycled emulsion.

After extraction from the emulsion well, the emulsion may be transported to a detection system or region configured to detect the amplification of a target in the droplets of the emulsion, for example, by detecting fluorescence radiation emitted by the droplets. In some cases, the sample-containing emulsion may be extracted from the emulsion well prior to thermocycling rather than after thermocycling, in which case the emulsion could be thermocycled while disposed within the extraction instrument or after being placed in another suitable container.

The following description presents further exemplary methods of operating droplet generation systems. The methods may be generally suitable for use with various droplet generation systems described herein, at least including any of the systems shown in FIGS. 1-9 and described in the accompanying text above and in Example 2 below. The steps presented below and elsewhere herein may be performed in any suitable order and in any suitable combination (including subcombinations consisting of a subset of the steps). In some embodiments, steps may be repeated. Furthermore, the steps may be combined with and/or modified by any other suitable steps, aspects, and/features of the present disclosure. The following description refers to FIGS. 3-9 to indicate the state of an exemplary droplet generation system after various steps of the disclosed methods are performed, and to describe certain details of a suitable channel network that can be used in conjunction with the present methods.

Sample-containing fluid may be introduced through a sample port of a channel component (e.g., channel component 72) to a sample well (e.g., sample well 166; see FIG. 9A, step 220). In some embodiments, sample-containing fluid may be added directly to the sample well, before the channel component (and/or a base thereof, such as base 76) is joined with the well component, thereby bypassing the sample port. Sample may be added before or after attachment of a cap (e.g., cap 78) to a base of the channel component.

Carrier fluid may be transported through a carrier port of the channel component to a carrier well (e.g., see step 224 of FIG. 9A). In some embodiments, carrier fluid may be added directly to the carrier well, before the channel component is joined with the well component, thereby bypassing the carrier port. Carrier fluid may be added before or after attachment of the cap.

A cap may be disposed or applied over the top surface of the base of the channel component, to seal the top of apertures (e.g., ports and passages) and a channel network formed in the top surface of the base. In some cases, the top of the channel network already may be sealed with a first cap, in which case a second cap may be applied to cover and/or seal one or more apertures, such as at least one sample port. The cap may be pierced to open a carrier port in the channel component and thus to allow the ingress of air into the carrier well. The cap may be pierced to open and/or fluidically connect to a vacuum port in the channel component.

A vacuum source may be connected to the vacuum port. In some cases, the connection may be achieved at least in part by piercing a cap over the vacuum port. In some cases, the end of a vacuum conduit may be used to pierce the cap and access the vacuum port.

Negative pressure may be applied to the vacuum port by the vacuum source (e.g., see step 228 of FIG. 9B). This causes negative pressure in an inverted vacuum dripper of the channel component, such as vacuum tube 164 depicted in FIG. 9B, and thus in a vacuum channel of the channel network, such as vacuum channel 194 depicted in FIG. 5. Because the top of emulsion port 188 is sealed, this creates negative pressure in a droplet dripper of the chip component such as droplet tube 162 depicted in FIG. 9B, and thus in the channels of the droplet generator, as will now be described in more detail with reference again to FIGS. 5-8.

Negative pressure in droplet tube 162 causes negative pressure in both sample sipper 158 and carrier sipper 160 as follows. Exposed carrier port 186, which was opened in step 224 of FIG. 9A, allows the ingress of air through the carrier port and into carrier well 168, which forces carrier fluid through inverted carrier sipper 160 of the channel component and into the channel network. Furthermore, sample vent channel 192 provides fluid communication between the carrier port and the sample port, which allows the ingress of air through the sample port and forces sample-containing fluid through the inverted sample sipper tube and into the channel network.

More specifically, negative pressure in sample sipper 158 causes sample-containing fluid to be drawn from the sample sipper into the top region of sample passage 196, and from there into sample channel 174 of the channel network (see FIGS. 5 and 6). Similarly, negative pressure in carrier sipper 160 causes carrier fluid to be drawn from the carrier sipper into a top region of carrier passage 198, and from there into a pair of carrier fluid channels 176, 178 of the channel network. The sample-containing fluid and the carrier fluid drawn into the channel network meet at a cross-shaped droplet generation region, formed by channel junction 182.

Droplets of sample-containing fluid suspended in carrier fluid are generated at the droplet generation region, in a manner described previously. The cross-type droplet generation region shown in FIG. 5 is merely exemplary. In some cases, other configurations of the same number or a different number of intersecting channels may be used to generate droplets, and all such configurations are within the scope of the present disclosure.

The emulsion of generated droplets may be transported through a droplet channel 180 of the channel network to droplet passage 200, into droplet dripper 162, and into emulsion well 170.

One or more channels extending to the emulsion well may be deformed to fluidically isolate the emulsion well. For example, a heat stake may be applied to the channel network of the channel component, to fluidically isolate the emulsion well (e.g., see step 232 of FIG. 9B). Equivalently, one could describe this step as "heat staking" an appropriate region of the channel network. For example, a heat stake may be applied across droplet channel 180, sample vent channel 192, and vacuum channel 194, sealing the emulsion well from fluid communication with any other portion of the droplet generation system (see FIG. 5 for channel positions). As described previously, this prevents the generated droplets from passing back into the channel network and thus failing to reach the detection system for a subsequent detection step, and also from potentially contaminating other, reusable portions of the droplet generation system. The heat stake also protects droplets and/or carrier fluid from evaporation losses during thermal cycling.

The generated droplets are optionally thermocycled to amplify individual copies of one or more targets that may be contained within the droplets (e.g., see step 236 of FIG. 9B). Alternatively, droplets may be removed from the emulsion well and thermocycled (or otherwise treated) in another container.

The generated droplets are optionally removed from the emulsion well and transported to a detection region, where a detection system may be configured to detect photoluminescence (such as fluorescence) as the signature of the presence of one or more particular targets in the droplets. As mentioned previously, in some cases, the droplets may be thermocycled and/or transported to the detection system while still disposed in the emulsion well of the droplet generation system, whereas in other cases the droplets may be extracted from the emulsion well before thermocycling, or after thermocycling and before the detection step.

Many variations of microfluidic device 152 generally described above and depicted in FIGS. 3-9 are possible and fall within the scope of the present disclosure. For example, the well component may include any desired number of wells, such as 32, 96, or 384 wells, among others, allowing 8, 24, or 96 samples, respectively, to be processed into droplet form with a single system. Similarly, in some cases the channel component may include any desired number of ports and channel networks, allowing multiple samples to be handled with a single channel component. Furthermore, the precise dimensions and shapes of the apertures, wells, channel network, and other elements of the droplet generation system may be chosen for convenience and performance, and may be different for different applications of the system.

Example 2: Droplet Generation Device with Fluid Pickups and a Carrier Manifold

This example describes an exemplary embodiment 252 of microfluidic device 52 for fluid processing system 50 (see FIGS. 1, 2, 2A, and 2B). Device 252 is configured for generating an array of emulsions using a fixed, dedicated pickup tube for the sample of each emulsion. The device also has a carrier manifold that receives carrier fluid for all of the emulsions from an off-device (external) carrier reservoir that is fluidically connected to device 252; see FIGS. 10-18.

Figure 10:
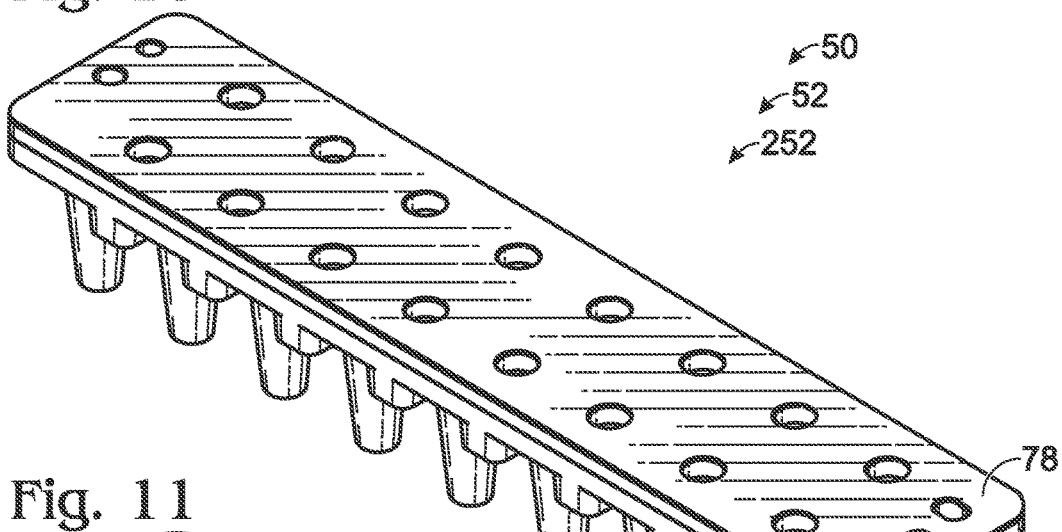
FIG. 10 is an isometric view of another exemplary embodiment of the microfluidic device of FIG. 1 constructed as a droplet generation device having an array of emulsion production units and including a channel component attached to and overlying a well component, in accordance with aspects of the present disclosure.
Figure 11:
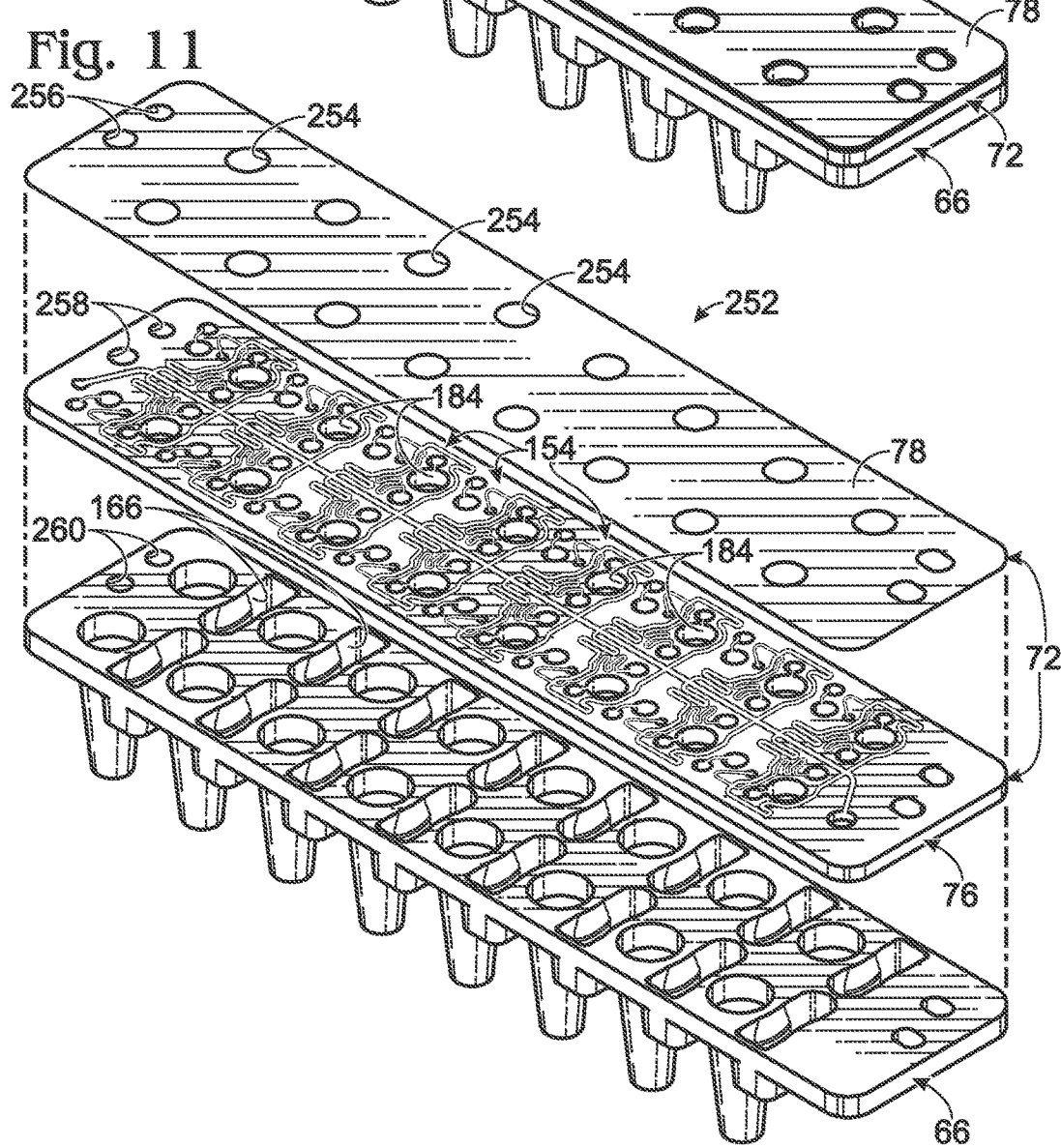
FIG. 11 is an exploded isometric view of the microfluidic device of FIG. 10.

FIGS. 10 and 11 show respective assembled and exploded views of device 252. The device may have any combination of the features described above in Section I and/or Example 1. For example, as described above for device 152, device 252 includes a sample-holding portion, namely, a well component 66 defining a plurality of wells. The device also includes a fluid-processing portion, namely, a channel component 72 attached to the well component and defining a plurality of channels, such as microchannels, that are fluidically connected to the wells. Elements of device 252 that functionally and/or structurally correspond to those of device 152 generally are identified using the same reference numbers as for device 152.

Channel component 72 has a base 76 and a cap 78 overlying the base. The cap may be attached to the base, and the base attached to well component 66, in any suitable order. In other words, channel component 72 may be assembled before or after base 76 is attached to well component 66. Channel component 72 provides an array of fluidically connected emulsion production units 154. In the depicted embodiment, the device has a two-by-eight array of units 154 in an SBS-compatible grid.

Cap 78 defines a plurality of pre-formed apertures 254 through which sample fluid may be introduced from a top side of device 252 to load the device with samples before sample-containing emulsions are formed. Each aperture 254 is aligned with a different sample well 166 of well component 66 and forms an opening for a sample port 184 defined by base 76 and aligned with the sample well. Apertures 254 may be closed with a cover after samples are introduced into the sample wells (e.g., see FIG. 9 above for device 152).

Cap 78 also may define one or more assembly openings 256 having counterpart assembly openings 258, 260 defined respectively by base 76 and well component 66. The assembly openings of the different parts may be aligned with one another to facilitate alignment of the parts during assembly when manufactured or by the end user. The openings also or alternatively may allow multiple copies of device 252 to be arrayed in a holder having pegs or other protrusions onto which the openings can be placed. The holder can position the device copies in an array having defined locations and spacings of the copies, and thus of all the sample wells (and emulsion wells) of the copies relative to one another.

Figure 12:
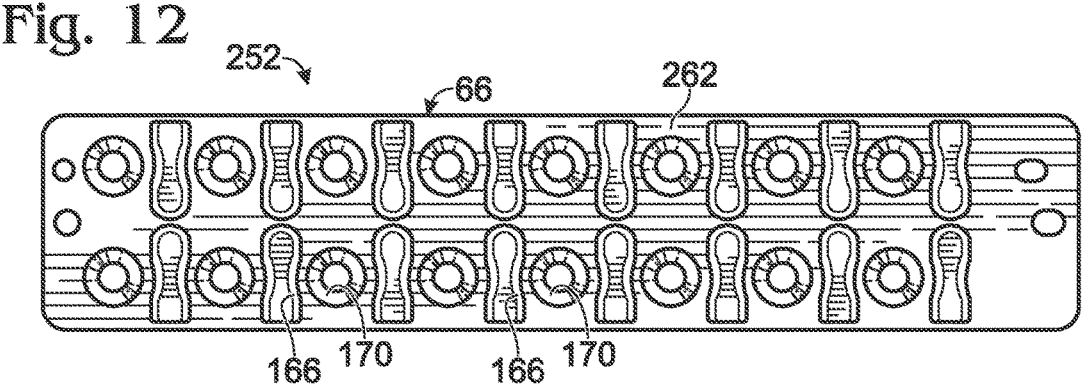
FIG. 12 is a plan view of the well component of the device of FIG. 10.

FIG. 12 shows a top view of well component 66. The well component defines a sample well 166 and an emulsion well 170 under each emulsion production unit 154 (also see FIG. 11). Each well may have any suitable shape. For example, in the depicted embodiment, each sample well is elongated horizontally and each emulsion well is conical. The wells are formed in a top surface 262 of well component 66, which may be a planar top surface for attachment in a fluid-tight seal to base 76. Well component 66 of device 252 has no carrier wells (compare with device 152 of FIGS. 3-9).

Figure 13:
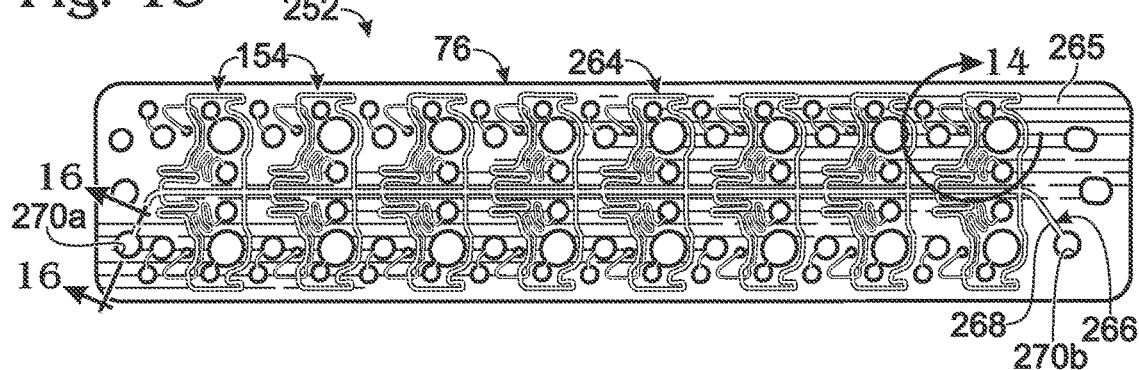
FIG. 13 is a plan view of a base of the channel component of the device of FIG. 10, taken in the absence of a cap of the channel component.
Figure 14:
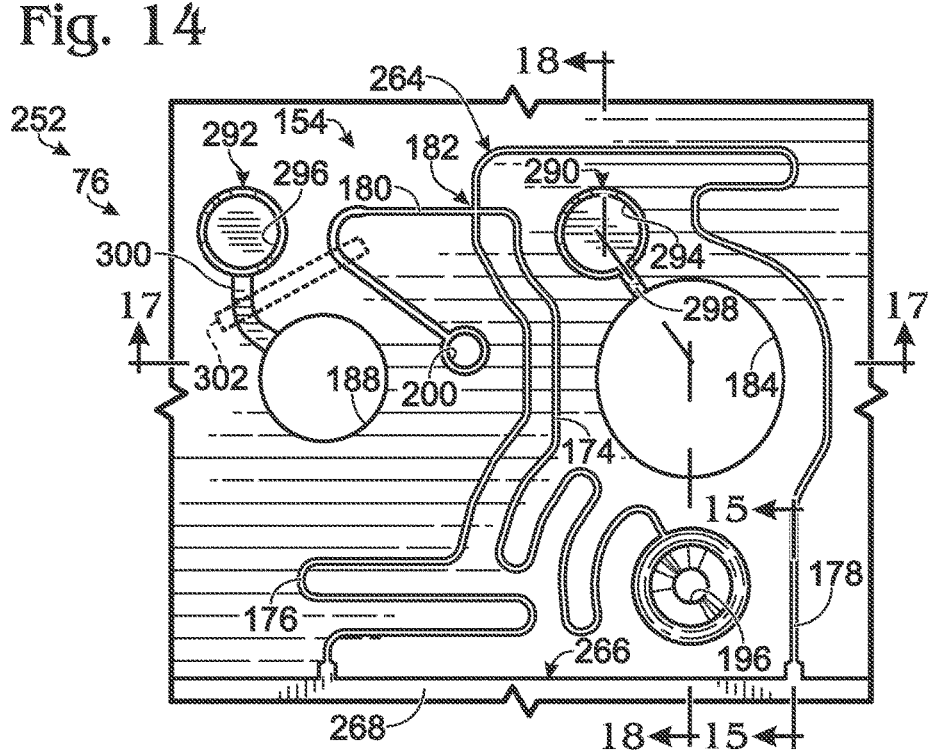
FIG. 14 is a fragmentary plan view of a single emulsion production unit of the device of FIG. 10, taken generally around the region indicated at "14" in FIG. 13 in the absence of the cap.
Figure 15:
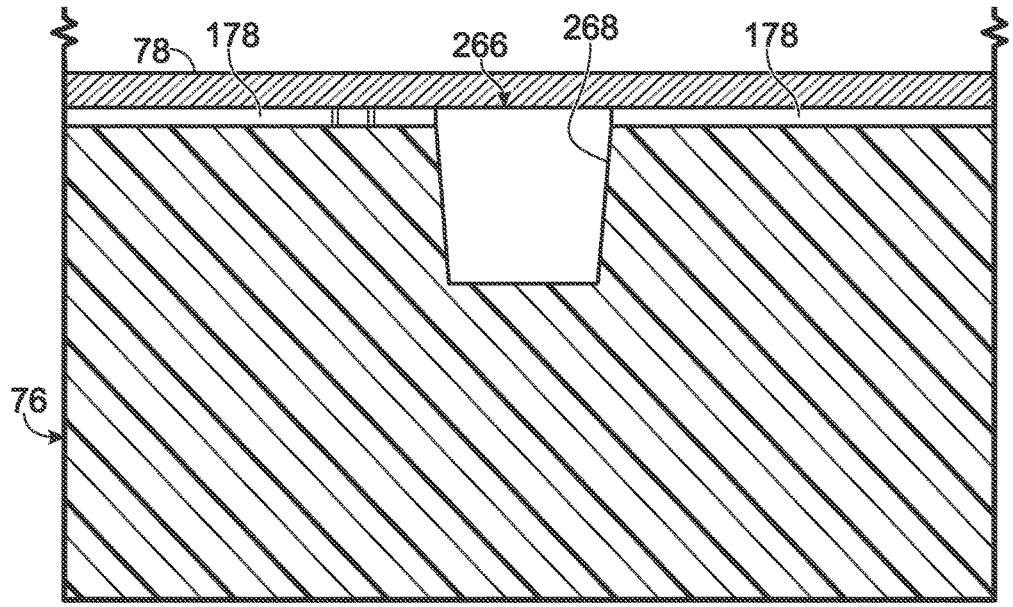
FIG. 15 is a fragmentary sectional view of the channel component of the device of FIG. 10, taken generally along line 15-15 of FIG. 14 (but with mirror-image symmetry) through a carrier manifold and a pair of carrier channels that extend from the carrier manifold to a pair of emulsion production units.

FIGS. 13-15 show various views of base 76. The base has a channel network 264 formed in a top surface 265 of the base. In other embodiments, the channel network may be formed in a bottom surface of cap 78 (e.g., see FIGS. 2A and 2B). Channel network 264 forms emulsion production units 154 as a fluidically interconnected set. (One of the emulsion production units is shown in FIG. 14.) The fluid interconnection of units 154 of device 254 is in contrast to device 152 of Example 1, which provides an array of fluidically isolated channel networks 156 (see Example 1). More particularly, the emulsion production units of device 252 are each fluidically connected to a carrier manifold 266 of channel network 264). In the depicted embodiment, the carrier manifold includes a larger (wider/deeper) supply channel 268 of the channel network that extends longitudinally on the top surface of base 76, between the two rows of emulsion production units 154. The carrier manifold connects along its length to lateral branch channels of the channel network, namely, a pair of carrier channels 176, 178 of each emulsion production unit 154 (see FIG. 14). In other embodiments, only one carrier channel (or three or more carrier channels) may extend from the carrier manifold to each emulsion production unit. In other embodiments, the carrier manifold may include a branched supply channel configuration with branches each connected to a subset of the carrier channels of the device.

Carrier manifold 266 is connectable to an external source of carrier fluid via at least one carrier port. In the depicted embodiment, the opposite ends of carrier manifold 266 form carrier ports 270a, 270b (see FIG. 13). However, the carrier manifold may form any suitable number of carrier ports at any suitable positions along the carrier manifold. Furthermore, the device may have any suitable number of distinct and/or separate carrier manifolds.

The carrier ports may be used in any suitable manner. In some embodiments, only one of the carrier ports may be connected to a source of carrier fluid during performance of a method of forming droplets with device 252. The user may be permitted to select which carrier port is utilized for introduction of carrier fluid into device 252. The other carrier port may be left closed and may provide a region where trapped air can collect without interfering with droplet generation. Alternatively, a first carrier port may be connected to a source of carrier fluid and a second carrier port may be open or opened to permit pre-loading of the carrier manifold with carrier fluid. In this case, carrier fluid is received in the carrier manifold via the first carrier port, and air and/or excess carrier fluid may leave the carrier manifold via the second carrier port. The second carrier port may be sealed after a pre-loading operation and before application of vacuum or pressure to drive droplet generation. In some embodiments, two or more carrier ports may be connected to the same source of carrier fluid, to allow the carrier fluid to enter a channel network via two or more distinct carrier ports.

Figure 16:
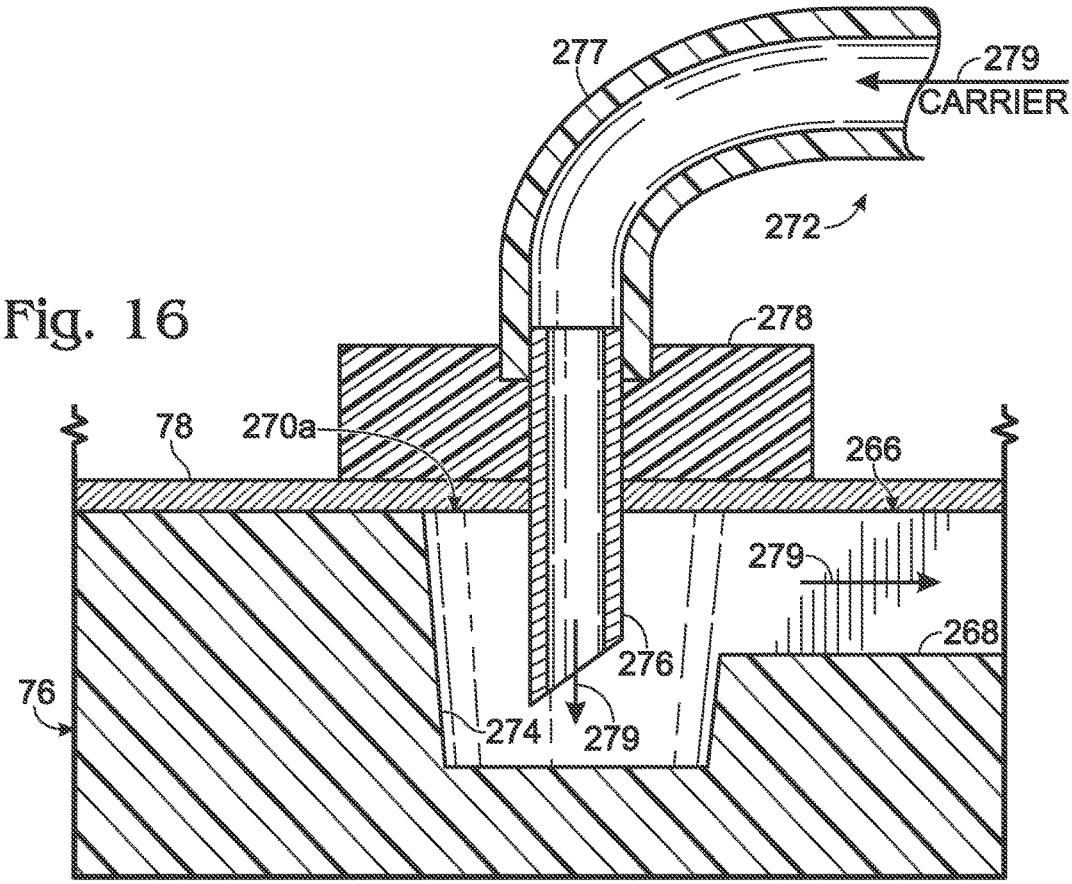
FIG. 16 is a fragmentary sectional view of the channel component of the device of FIG. 10 connected to a source of carrier fluid, taken generally along line 16-16 of FIG. 14 through a carrier port of the device and illustrating a path for flow of carrier fluid into a channel network of the device without passing through the bottom side of the channel component, in accordance with aspects of the present disclosure.

FIG. 16 shows a sectional view of carrier port 270a fluidically connected to an external source 272 of carrier fluid 116. The port may include a blind hole 274 formed in the top surface of base 76 and communicating laterally with supply channel 268 of the carrier manifold. Blind hole 274 may be wider and/or deeper than supply channel 268. In other embodiments, supply channel 268 may widen or deepen at any suitable positions along its length to form one or more carrier ports, and/or the supply channel may be accessed at an arbitrary position along its length to provide a carrier port. Carrier manifold 266, including the carrier ports, may be sealed at the top with cap 78. The cap may be pierced at any time over a carrier port with a hollow piercing element 276 that is fluidically connected to the external source of carrier fluid, such as via a conduit 277. Piercing element 276 may be connected to and/or integrally formed with a gasket 278 capable of forming a fluid-tight seal with cap 78 around the piercing element. As a result, the external source of carrier fluid is fluidically connected to carrier manifold 266 via carrier port 270a, allowing carrier fluid to be pushed and/or pulled into the carrier manifold, indicated by flow arrows at 279.

FIG. 14 shows the channels and apertures of one of emulsion production units 154. The unit has a similar channel structure to that of device 152 (e.g., see FIG. 5). A channel junction 182 that functions as a site for droplet generation is formed where a sample channel 174 and carrier channels 176, 178 meet a droplet channel 180. The unit, as in device 152, also has a sample port 184 for addition of sample to a sample well, and an emulsion port 188 for removal of emulsion from an emulsion well after the emulsion has been collected in the emulsion well, with each port formed as a through-hole in base 76. However, the unit has no corresponding carrier port. Instead, carrier fluid is supplied from a connected, off-device source. Furthermore, the emulsion production unit, as in device 152, has a sample passage 196 that directs sample upward from an underlying sample well to sample channel 174, and a droplet passage 200 that directs droplets in carrier fluid from droplet channel 180 downward to an underlying emulsion well.

Figure 17:
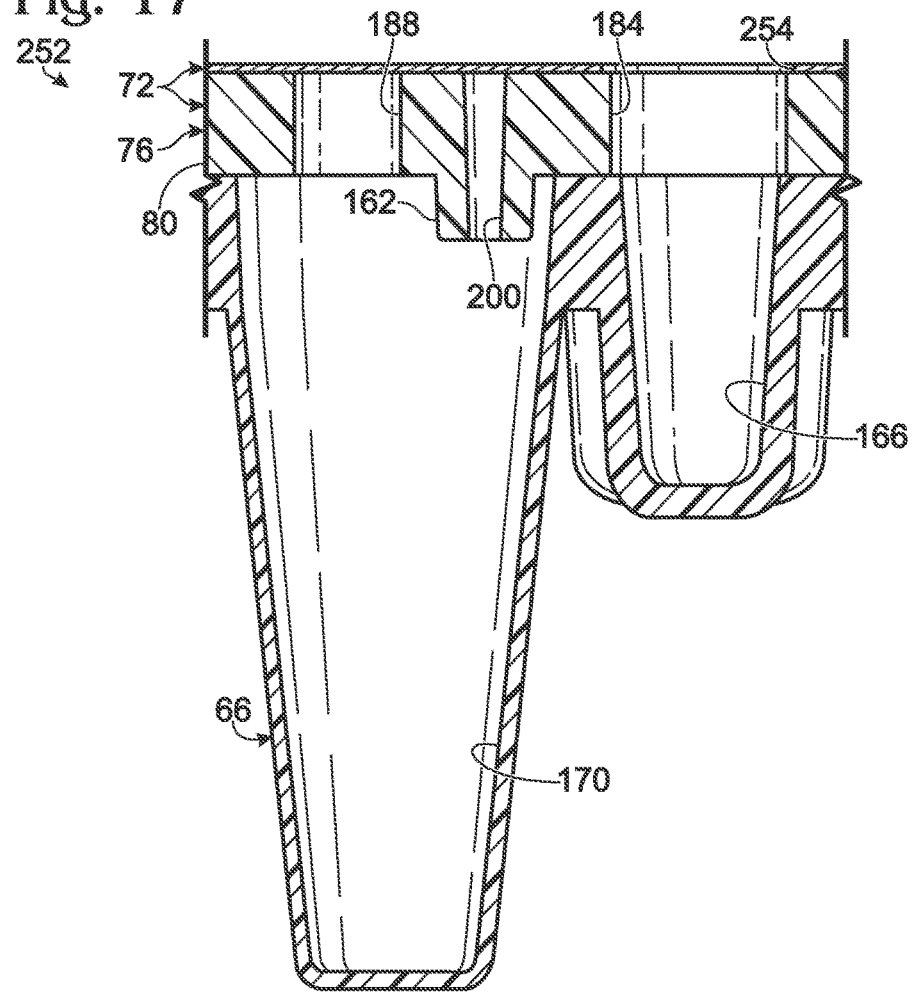
FIG. 17 is a sectional view of a single emulsion production unit of the device of FIG. 10, taken generally along line 17-17 of FIG. 14 in the presence of the cap.

FIG. 17 shows a sectional view taken through a sample well 166 and an emulsion well 170 of device 252. (The channels are too small to be visible in this view.) A droplet tube 162 projects into emulsion well 170 from a body 80 of base 76. The droplet tube is very short, to minimize the chance of collected emulsion re-entering the droplet tube. Droplet passage 200 extends upward through tube 162 to the channel network.

Figure 18:
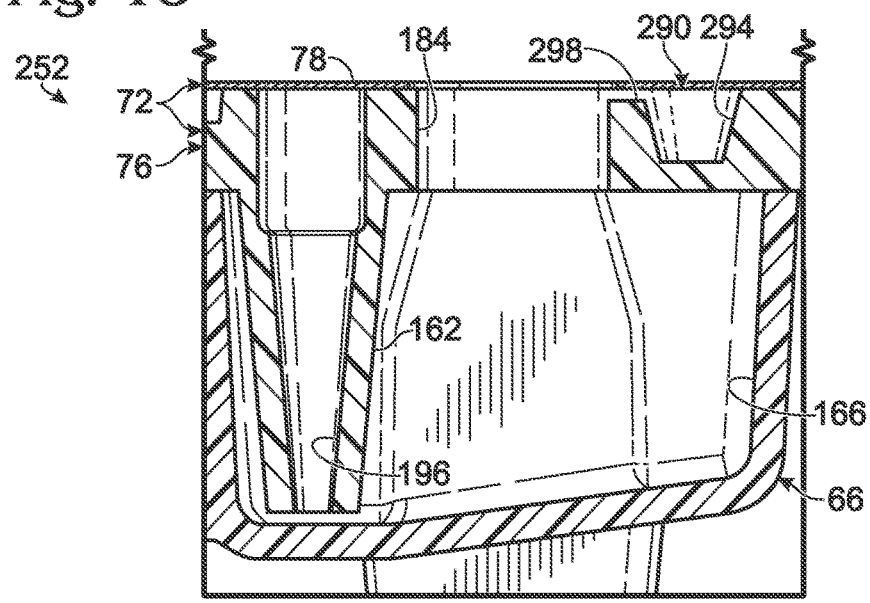
FIG. 18 is another sectional view of the single emulsion production unit of the device of FIG. 10, taken generally along line 18-18 of FIG. 14 in the presence of the cap.

FIG. 18 shows a sectional view taken through a sample well 166. The sample well is asymmetrically shaped, with a deeper end on the left and a shallower end on the right. Sample tube 162 is extends downward to a position near the bottom of the sample well at the deeper end thereof. Configuring the sample well to be relatively wide and shallow, as depicted here, allows sample tube 162 to be shorter and fatter. As a result, the sample tube can be injection molded integrally with the rest of base 76.

Sample port 184 and emulsion port 188 each are connected to an associated port, namely, a vent port 290 and a vacuum port 292, respectively (see FIGS. 14 and 18). Each of ports 290 and 292 is created by a respective blind hole 294, 296 formed in the top surface of base 76 and connected to port 184 or 188 by a respective channel 298 or 300.

Vent port 290 provides a site for venting sample well 166 after the well has been loaded and aperture 254 has been sealed with a cover (also see FIGS. 10 and 11). Cap 78 can be pierced over vent port 290 with a piercing element to open the port and thus vent the sample well before emulsion formation begins. Vent port 290 is spaced from sample port 184 by channel 298, which reduces the chance of contamination of the piercing element with sample when the sample well is vented.

Vacuum port 292 is similar in structure to vent port 290 and provides a site for connecting a vacuum source to the underlying emulsion well via emulsion port 188. The vacuum port is spaced from emulsion port 188 by channel 300, which reduces the chance of contaminating the vacuum system with emulsion when the cap is pierced over vacuum port 292 to connect the vacuum source to device 252 and/or when vacuum is applied. Channel 300 also allows sealing the emulsion well, after the emulsion is generated, by closing off channel 300 through channel deformation, such as via heat staking through application of heat and, optionally, pressure. Channels 180 and 300 may extend close to each other, to enable heat staking them at the same time in a single operation, such as at a heat stake area 302 extending across both channels, thereby completely sealing the emulsion well after emulsion generation and before thermal cycling. Alternatively, channels 180 and 300 may be heat staked separately at the same or different times. Heat staking channels 180 and 300 at heat stake area 302 is analogous to heat stake 234 described above for the last configuration shown in FIG. 9B.

Example 3: Exemplary Instrument to Interface with a Microfluidic Device

Figure 19:
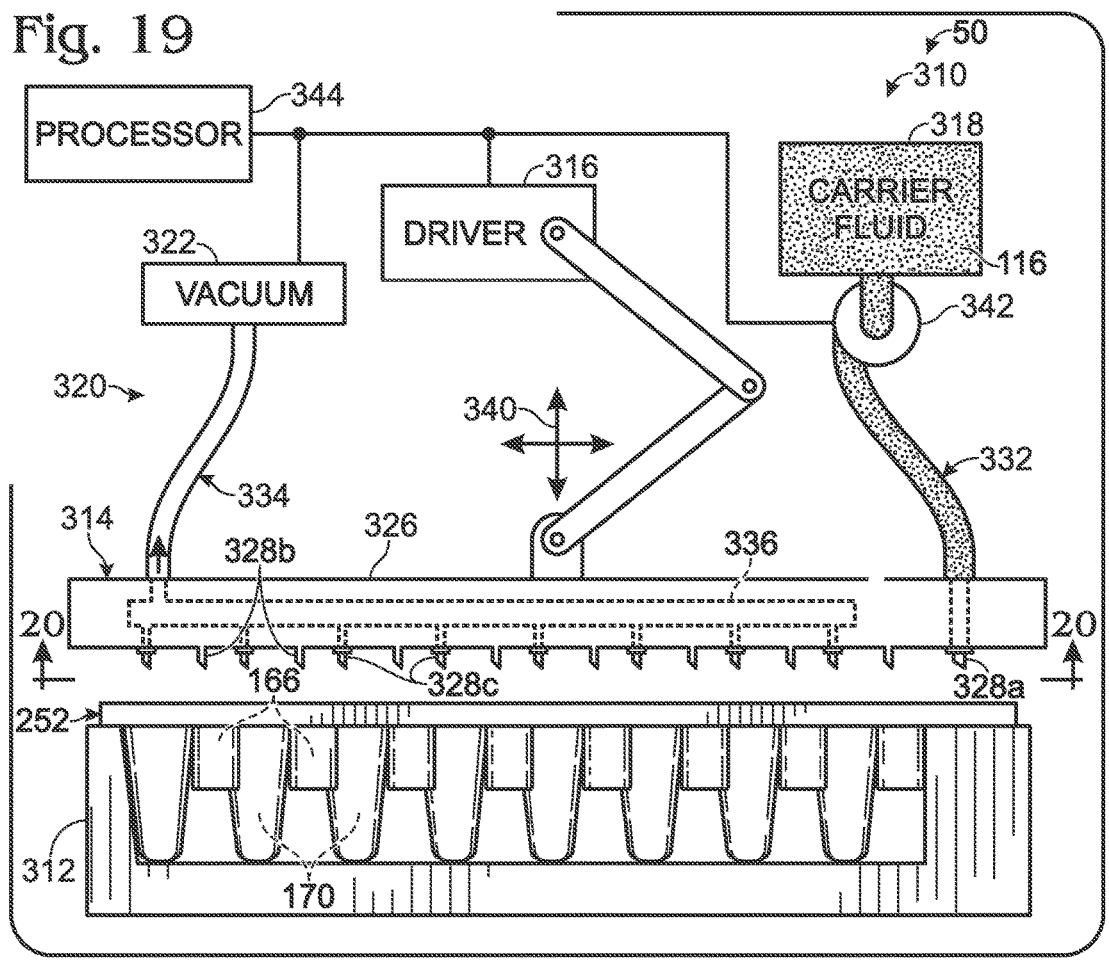
FIG. 19 is a schematic view of an exemplary instrument for driving fluid flow for droplet generation within the device of FIG. 10, taken with the instrument holding the device of FIG. 10 but not yet fluidically connected to the device, and with the device viewed at elevation, in accordance with aspects of the present disclosure.
Figure 20:
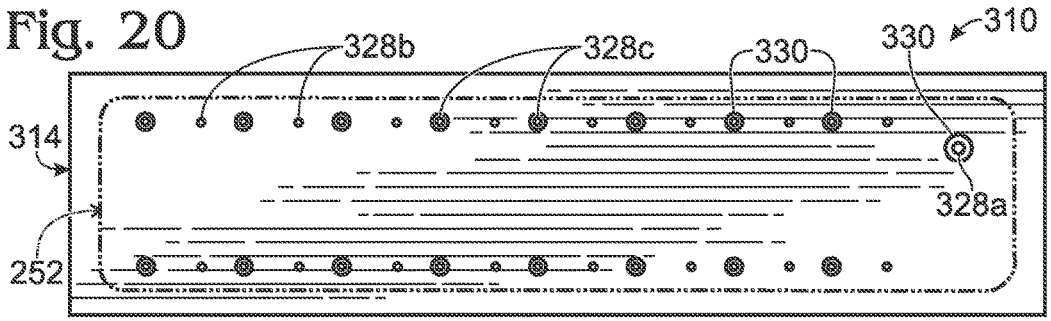
FIG. 20 is a bottom view of a head of the instrument of FIG. 19, taken generally along line 20-20 of FIG. 19.
Figure 21:
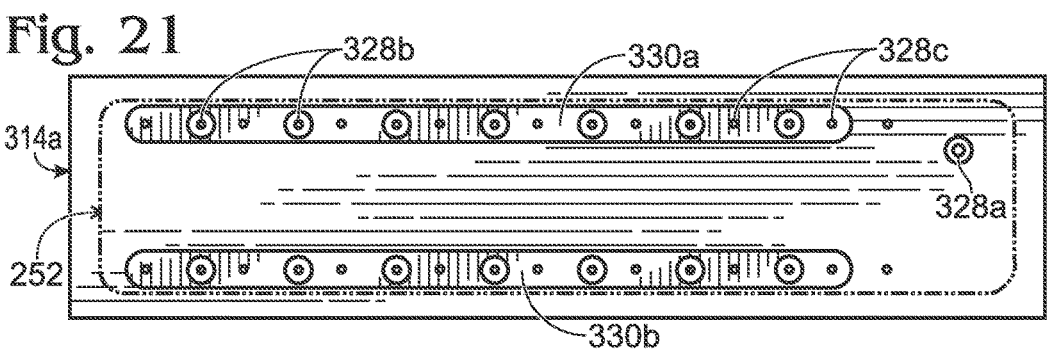
FIG. 21 is a bottom view of another exemplary head for the instrument of FIG. 19, taken as in FIG. 20.

This example describes an exemplary instrument 310 configured to fluidically connect to microfluidic device 252 and exemplary methods of using the instrument to generate emulsions; see FIGS. 19-21.

FIGS. 19 and 20 show instrument 310 of microfluidic system 50 for driving and controlling fluid flow within device 252. Instrument 310 may be configured for use with any of the microfluidic devices disclosed herein. Any or all of the operations performed automatically by instrument 310 alternatively may be performed manually by a user.

Instrument 310 may include a support 312 to hold and position device 252 with respect to at least one processing head 314. Processing head 314 is positioned or positionable over device 252, in alignment with the device, and is configured to interface with the top side of device 252. In the configuration depicted in FIG. 19, the processing head is in a pre-processing, ready position over device 252, before fluid processing has been initiated and with processing head 314 not yet in contact with the device. The processing head may be operatively connected to a drive mechanism 316 (a "driver"), a carrier fluid reservoir 318 containing carrier fluid 116, and a vacuum source 320 including a vacuum pump 322 (or other source of vacuum or pressure). A frame may provide sites for attachment, organization, and/or support of other structures of the instrument.

Processing head 314 has a body 326 and a plurality of piercing elements connected to the body (see FIGS. 19 and 20). The piercing elements may be vertically aligned or alignable with various ports of device 252 to allow the piercing elements to pierce the cover over the port. Piercing the cover opens the port, such as to form a vent or fluidically connect the port to carrier fluid reservoir 318 or vacuum source 320.

The piercing elements may be categorized as distinct types, namely, carrier piercing element(s) 328a, vent piercing elements 328b, and vacuum piercing elements 328c according to the type of port opened by the element. One or more of these types may be arrayed to match the arrangement of corresponding ports of device 252, as illustrated by comparing FIGS. 13 and 14 with FIG. 20. At least one carrier piercing element 328a may be aligned or alignable with at least one carrier port 270a or 270b (port 270b is aligned in this example). A plurality of vent piercing elements 328b may be aligned or alignable with a corresponding plurality of vent ports 290. (All of the vent piercing elements are aligned with all the vent ports in this example). A plurality of vacuum piercing elements 328c may be aligned or alignable with a corresponding plurality of vacuum ports 292. (All of the vacuum piercing elements are aligned with all of the vacuum ports in this example.) Accordingly, processing head 314 and device 252 may be moved vertically relative to one another to pierce two or more types of ports at the same time. In some embodiments, two or more types of ports may be pierced at different times. For example, the vent ports may be pierced at a different time, such as before or after, the vacuum ports and/or the carrier port(s). As another example, the carrier port(s) may be pierced at a different time than the vacuum port (e.g., to pre-load the carrier manifold with carrier fluid). Furthermore, the ports of a given type may be pierced as two or more sets at different times. Ports may be pierced at different times using, for example, a horizontally positionable processing head with fewer piercing elements, two or more processing heads (e.g., different heads for the vent ports and the vacuum ports), or a separate tool to manually pierce some of the ports (e.g., the vent ports), among others.

Piercing elements 328a, 328b, and 328c may be on the same processing head 314 or different processing heads 314 of the instrument. In some embodiments, one or more of the sets of piercing elements may be arranged in an array that matches an array defined by all or a subset of ports of the device. For example, piercing elements 328b may be arranged in an array that matches an arrangement of two or more vent ports 290 of the device. In some embodiments, piercing elements 328b may be configured to pierce a plurality of vent ports 290 at the same time, such as each vent port 290 of the device. Piercing elements 328c may be arranged in an array that matches an arrangement of two or more vacuum ports 294 of the device. In some embodiments, piercing elements 328c may be configured to pierce a plurality of vacuum ports 294 at the same time, such as each vacuum port 294 of the device. In some embodiments, piercing elements 328b and 328c may be arranged to pierce a plurality of vent ports 290 and a plurality of vacuum ports 294 at the same time. In some embodiments, piercing elements 328a and 328c may be arranged to pierce at least one carrier port 270a or 270b and a plurality of vacuum ports at the same time.

Each piercing element may be associated with a gasket 330, which may be dedicated to the piercing element or shared among two or more piercing elements (see below). Each piercing element may be hollow or solid.

Carrier piercing element(s) 328a may be connected to carrier fluid source 318, indicated by an arrow at 332. Accordingly, each carrier piercing element 328a may fluidically connect the carrier fluid source to carrier manifold 266 when piercing element 328a enters the carrier port.

Vent piercing element(s) 328b may create fluid communication with the atmosphere. Accordingly, each vent piercing element 328b may function to connect ambient air outside the device with a vent port 290 and its associated sample well when piercing element 328b opens the vent port (e.g., after the sample port has been covered).

Vacuum piercing element(s) 328c may be connected to vacuum source 320, indicated by an arrow at 334. Accordingly, each piercing element 328c may fluidically connect the vacuum pump to a vacuum port (and its associated emulsion well) when the piercing element enters the vacuum port. Head 312 may include a vacuum manifold 336 through which the vacuum piercing elements communicate with a vacuum source.

Drive mechanism 316 moves support 312 and head 314 relative to one another. In the depicted embodiment, the drive mechanism causes head 314 to move while support 312 remains stationary. In other embodiments, the drive mechanism may cause support 312 to move while head 314 remains stationary, among others. The drive mechanism may move head 314 in only one dimension, namely, along a vertical axis, such as if the head can perform all of its functions in one position on the device. Alternatively, the drive mechanism may move head 314 in two or three dimensions, indicated at 340, which may permit the head to be positioned on the device a plurality of times to perform different functions and/or to perform the same function multiple times for different subsets of the emulsion production units (e.g., to produce emulsions from different subsets of the units in sequence).

The instrument also may be configured to deform channels of device 252, such as by heat staking, to block passage of fluid through the channels. For example, the instrument may have a one or more heating elements that can be pressed against the top side of device 252 after emulsion formation to seal each emulsion well by blocking a channel 180 and a channel 300 associated with the emulsion well (see FIG. 14). Accordingly, the heating elements may be arranged in an array that matches the spacing of the emulsion production units, and more particularly, in an array that matches and is alignable with an array of heat stake areas 302 defined by channel pairs 180 and 300 (see FIG. 14). The heating elements may be present on head 314 or a different head of the instrument, or may be provided by a different instrument. In any event, the emulsions may be fluidically isolated in the emulsion wells by channel deformation and then thermally cycled within the wells. In some embodiments, a laser may be used to deform the channels.

Carrier fluid reservoir 318 may be vented to allow vacuum pump 322 to pull carrier fluid into device 252 from the reservoir. Alternatively, or in addition, the carrier fluid reservoir may be connected to an optional carrier pump 342 that drives carrier fluid 116 from the reservoir into the device, optionally with assistance from vacuum source 320. The carrier pump generally is not needed unless it is used to pre-load carrier fluid into the device prior to application of vacuum with the vacuum source.

Instrument 310 further may include a processor 344 (interchangeably termed a controller) in communication with any combination of drive mechanism 316, vacuum pump 322 and/or a valve and/or a pressure gauge therefor, and/or carrier pump 342, among others. The processor may control and coordinate fluid processing within device 252.

FIG. 21 shows another exemplary processing head 314a for instrument 310. Head 314a differs from head 314 in having gaskets 330a, 330b that are each shared by a plurality of vacuum piercing elements 328c. In some embodiments, the gasket may be formed integrally with one or more piercing elements.

Emulsions may be prepared with device 252 as follows. The steps presented below may be performed in any suitable order and combination, and each may be performed by the user or instrument 310, as described. Figures showing structures involved in particular steps are referenced below.

A sample may be loaded into each of sample wells 166 (see FIGS. 10 and 11). Replicates of the sample or different samples may be loaded into the wells. Each sample may be introduced into a sample well through an aperture 254 of cap 78 and a sample port 184 of base 76 and/or body 80 (see FIGS. 10, 11, and 14).

Sample ports 184 may be covered by application of at least one cover. One or more covers may be placed over the sample ports, which may (or may not) be attached to cap 78 and may (or may not) seal each sample port. Covering each sample port may reduce the chance of cross-contamination among the sample wells. In some embodiments, the sample ports may be left uncovered, covered loosely, or covered with a pre-perforated cover, among others, which may obviate the need for piercing a vent port for the sample well.

Device 252 may be placed onto support 312 of instrument 310. In some embodiments, vent ports 290 may be pierced (e.g., with a separate tool) before the device is placed onto the support. In some embodiments, the vent ports may be open when supplied to the user (e.g., pierced by the manufacturer or left uncovered when manufactured).

Processing head 314 and device 252 may be moved relative to each other to pierce a cover (composed of one or more layers) over ports, which may connect a source of carrier fluid, such as carrier reservoir 318, to one or more carrier ports, and/or connect vacuum source 320 to one or more vacuum ports.

Vacuum may be applied to device 252 with vacuum source 320 to drive emulsion formation. The vacuum may, for example, be applied by opening a valve of the vacuum source to connect the vacuum pump and/or a vacuum chamber to each vacuum port of device to 252. The applied vacuum draws carrier fluid into carrier manifold 266 and into each of carrier channels 176, 178 of each emulsion production unit 154 (see FIG. 14). The applied vacuum also draws sample fluid from each sample well into a sample channel 174. The channel network is designed to provide greater fluid impedance for sample travel to each channel junction 182 relative to carrier fluid travel to the channel junction, such that the carrier fluid reaches the channel junction first. This arrangement ensures that all of the sample in the emulsion is encapsulated by the carrier fluid, if sufficient carrier fluid is supplied to the channel junction. The resulting emulsion formed by each emulsion production unit 154 is collected in a respective emulsion well 170 (see FIGS. 11-14). Each emulsion can be removed from the emulsion well via the emulsion port after piercing cap 78, or piercing the emulsion port may be unnecessary if the emulsion port is not covered during emulsion formation.

Further aspects of exemplary instruments to drive and control droplet generation and exemplary methods of droplet generation that may be suitable for the fluid processing systems of the present disclosure are described in the patent documents listed above under Cross-References, which are incorporated herein by reference.

Example 4: Selected Embodiments I

This section describes further embodiments of systems and methods for droplet generation, presented without limitation as a series of numbered paragraphs.

1. A system for producing droplets, comprising: (A) a well component including a sample well, a carrier fluid well, and a emulsion well; and (B) a chip component configured to be attached to the well component and including a sample port configured to provide access to the sample well when the chip component is attached to the well component, a carrier fluid port configured to provide access to the carrier fluid well when the chip component is attached to the well component, a droplet port configured to provide access to the emulsion well when the chip component is attached to the well component, a first aperture leading into a first hollow protrusion configured to extend into the sample well when the chip component is attached to the well component, a second aperture leading into a second hollow protrusion configured to extend into the carrier fluid well when the chip component is attached to the well component, a third aperture leading into a third hollow protrusion configured to extend into the emulsion well when the chip component is attached to the well component, and a channel network configured to receive sample-containing fluid from the sample well via the first hollow protrusion, to receive carrier fluid from the carrier fluid well via second hollow protrusion, to generate an emulsion of sample-containing droplets suspended in carrier fluid, and to transport the emulsion to the emulsion well via the third hollow protrusion.

2. The system of paragraph 1, further comprising a penetrable cover configured to be applied over a top surface of the chip component.

3. The system of paragraph 1, wherein the well component further includes a vacuum well and the chip component further includes a vacuum port configured to provide access to the vacuum well when the chip component is attached to the well component, and a fourth aperture leading into a fourth hollow protrusion configured to extend into the vacuum well when the chip component is attached to the well component, and wherein the channel network is configured to generate the emulsion in response to negative pressure applied at the vacuum port and communicated to the channel network via the fourth hollow protrusion.

4. The system of paragraph 3, further comprising a vacuum source configured to fit within the vacuum port and to apply negative pressure to the channel network.

5. The system of paragraph 3, wherein the channel network includes a vacuum channel configured to communicate vacuum pressure from the vacuum well to the emulsion well.

6. The system of paragraph 1, wherein the chip component includes a substantially planar substrate, and wherein the channel network is substantially planar and is disposed within the substrate.

7. The system of paragraph 6, wherein the channel network includes a sample vent channel configured to provide a passage for air from the carrier fluid port to the sample well.

8. The system of any of paragraphs 1 to 7, wherein the well component and droplet generation component are repeated to form a regular array, with pairs consisting of a well component and a vertically adjacent droplet generation component capable of producing distinct sets of droplets.

9. The system of paragraph 8, wherein the regular array is a microplate footprint.

10. A method of generating droplets, comprising: (A) processing a sample-containing fluid into (or adding a sample-containing fluid to) a sample well of a well component; (B) processing a carrier fluid into (or adding a carrier fluid to) a carrier fluid well of the well component; (C) applying a sealing member over a top surface of a droplet generation chip component attached to the well component; (D) piercing the sealing member to expose a carrier fluid port formed in the chip component and providing access to the carrier fluid well; (E) piercing the sealing member to expose a vacuum port formed in the chip component; (F)

inserting a vacuum source into the vacuum port; (G) applying negative pressure to the vacuum port with the vacuum source and thus causing sample-containing fluid to pass from the sample well into a channel network of the chip component via a first hollow protrusion extending from the chip component into the sample well, and causing carrier fluid to pass from the carrier fluid well into the channel network via a second hollow protrusion extending from the chip component into the carrier fluid well; (H) generating droplets of sample-containing fluid suspended in carrier fluid in a droplet generation region of the chip component; and (I) processing the droplets to a emulsion well of the well component.

11. The system of paragraph 10, wherein the droplets are transported from the chip component to the emulsion well via a third hollow protrusion extending from the chip component into the emulsion well.

12. The system of paragraph 11, wherein the vacuum port provides access to a vacuum well of the well component, and wherein negative pressure applied to the vacuum port is communicated to the chip component via a fourth hollow protrusion extending from the chip component into the vacuum well.

13. The system of paragraph 10, further comprising fluidically isolating the emulsion well from the other wells of the well component, after processing the droplets to the emulsion well.

14. The system of paragraph 13, wherein fluidically isolating the emulsion well includes applying a heat stake to a portion of the channel network.

15. The system of paragraph 13, further comprising thermocycling the droplets to cause amplification of target molecules present in the droplets, and detecting fluorescence radiation emitted by the amplified target molecules.

16. The system of paragraph 10, wherein piercing the sealing member to expose the vacuum port is performed by the vacuum source.

17. The system of paragraph 10, wherein the step of adding a sample to a sample well is performed after the step of applying a sealing member.

18. The system of paragraph 17, wherein the step of adding a sample includes piercing the sealing member to obtain access to the sample well.

19. A method of generating droplets, comprising: (A) selecting a system comprising a droplet generation component, for generating droplets, and a well component, for holding a sample-containing fluid in a sample well, a carrier fluid in a carrier well, and droplets in a emulsion well, wherein the droplet generation component is positioned above the well component, and wherein there is sample-containing fluid in the sample well and carrier fluid in the carrier well; (B) drawing sample-containing fluid and carrier fluid up, against gravity, from the sample well and the carrier well, respectively, to the droplet generation component; (C) producing droplets from the sample-containing fluid and carrier fluid with the droplet generation component; and (D) depositing the droplets down, in the direction of gravity, into the emulsion well.

20. The method of paragraph 20, wherein the sample-containing fluid and the carrier fluid are drawn up to the droplet generation component by respective input tubes, optionally due to the application of vacuum.

21. The method of paragraph 19 or 20, wherein the droplets are deposited down into the emulsion well through an output tube.

22. The method of paragraph 21, wherein the droplet tube is disposed above the emulsion well and dimensioned such that the droplet tube does not contact the droplets once they have been deposited in the emulsion well.

23. The method of any of paragraphs 19 to 22, wherein the input tubes for the sample-containing fluid and the carrier fluid are disposed above the sample-containing fluid and the carrier fluid, and dimensioned to maintain contact with the sample-containing fluid and carrier fluid during production of droplets.

24. The method of any of paragraphs 19 to 23, wherein the droplets drip or fall into the emulsion well.

25. The method of any of paragraphs 19 to 24, wherein the system comprises the system of any of paragraphs 1 to 9.

Example 5: Selected Embodiments II

This section describes further embodiments of systems and method for fluid processing and/or droplet generation, presented without limitation as a series of numbered paragraphs.

1. A system for fluid processing, comprising: (A) a well; and (B) a channel component including (i) a body including a bottom surface attached to the well and a top surface having a microchannel formed therein, (ii) an input tube projecting into the well from the bottom surface of the body, and (iii) a passage extending through the input tube and the body, wherein the system is configured to receive a sample-containing fluid in the well such that the sample-containing fluid is in contact with a bottom end of the passage and is retained, with assistance from gravity, below a top end of the passage and out of contact with the microchannel until a pressure differential is created that drives at least a portion of the sample-containing fluid from the well via the passage and through the microchannel.

2. The system of paragraph 1, wherein the well is an input well, further comprising an output well disposed under the channel component, and wherein system is configured such that the pressure differential drives at least a portion of the sample-containing fluid from the input well to the output well.

3. The system of paragraph 2, wherein the input well and the output well are formed integrally with one another and separately from the body and the input tube.

4. The system of paragraph 2 or paragraph 3, wherein the body and the input tube are molded as a single piece, and wherein the input well and the output well are molded as another single piece.

5. The system of any of paragraphs 2 to 4, wherein the channel component has a channel network formed in the top surface of the body, and wherein the channel network is configured to receive at least a portion of the sample-containing fluid and to generate sample-containing droplets for collection in the output well.

6. The system of paragraph 5, further comprising a plurality of input wells and a plurality of output wells, wherein the channel component is configured to form a plurality of emulsions from at least one sample-containing fluid disposed in the plurality of input wells and to direct the plurality of emulsions to the plurality of output wells.

7. The system of paragraph 6, wherein each emulsion includes a same carrier fluid that forms a continuous phase of the emulsion, and wherein the channel network includes a manifold that supplies the same carrier fluid for each emulsion.

8. The system of any of paragraphs 1 to 7, wherein the channel component includes a carrier port connected to the channel network and configured to receive a carrier fluid that enters the carrier port from above the channel component in response to the pressure differential.

9. The system of any of paragraphs 1 to 8, wherein the channel component includes a cover disposed on the top surface of the body, further comprising an instrument configured to pierce the cover and apply a vacuum or pressure to the channel component through the pierced cover to drive flow of the sample-containing fluid from the well and through the microchannel.

10. The system of any of paragraphs 1 to 9, wherein the body and the input tube are formed integrally with one another and separately from the well.

11. The system of any of paragraphs 1 to 10, wherein the channel component defines a sample port over the well and separate from the passage for introduction of the sample-containing fluid into the well.

12. The system of any of paragraphs 1 to 11, wherein the channel component includes a cover attached in a fluid-tight seal to the top surface of the body and providing a top wall for the microchannel.

13. The system of paragraph 12, wherein the channel component includes at least one port covered by the cover and configured to be accessed by piercing the cover.

14. The system of any of paragraphs 1 to 13, wherein the channel component includes a base including the body and the input tube and also includes a cover disposed on the base and at least partially covering each of a plurality of ports defined by the base and each fluidically connected to the microchannel.

15. A method of processing fluid, the method comprising: (A) dispensing a sample-containing fluid into a well through a sample port of a channel component including (i) a body having a bottom surface attached to the well and a top surface with a microchannel formed therein, (ii) an input tube projecting into the well from the bottom surface of the body, and (iii) a passage extending through the input tube and the body, wherein the dispensed sample-containing fluid is in contact with a bottom end of the passage and is retained, with assistance from gravity, below a top end of the passage and out of contact with the microchannel; and (B) creating a pressure differential that drives at least a portion of the sample-containing fluid from the well via the passage and through the microchannel.

16. The method of paragraph 15, wherein the step of creating a pressure differential causes at least a portion of the sample-containing fluid to travel downward through the body for collection by another well under the body.

17. The method of paragraph 15 or paragraph 16, wherein the body has a channel network formed in the top surface, and wherein the step of creating a pressure differential causes an emulsion of sample-containing droplets to be generated in the channel network.

18. The method of any of paragraphs 15 to 17, wherein the step of creating a pressure differential causes at least a portion of the emulsion to be collected in another well under the body.

19. The method of paragraph 17 or paragraph 18, wherein the step of dispensing a sample-containing fluid includes a step of dispensing at least one sample-containing fluid into each of a plurality of input wells disposed under the body, and wherein the step of creating a pressure differential causes a plurality of emulsions to be collected in a plurality of output wells disposed under the body.

20. The method of any of paragraphs 15 to 19, wherein the channel component includes a cover disposed on the top surface of the body and forming a top wall of the microchannel, and wherein the step of creating a pressure differential includes a step of applying a vacuum or pressure to the channel component at an opening defined by the cover.

21. The method of paragraph 19 or paragraph 20, wherein each of the plurality of emulsions is formed in a different region of the same channel network.

22. The method of any of paragraphs 19 to 21, wherein droplets of each emulsion are disposed in a carrier fluid that forms a continuous phase of the emulsion, and wherein at least a portion of the carrier fluid is supplied to the channel network from a carrier port of the channel component that receives the carrier fluid from a position over the carrier port in response to the pressure differential.

23. The method of any of paragraphs 15 to 22, wherein the step of creating a pressure differential includes a step of piercing a cover disposed on the top surface of the body to create an opening in the cover, and a step of applying a vacuum or pressure to the channel component at the opening.

24. The method of any of paragraphs 15 to 23, wherein the step of creating a pressure differential causes at least a portion of the sample-containing fluid to be collected in an output well, further comprising a step of deforming one or more channels that communicate with the output well to block fluid flow through the one or more channels and fluidically isolate the at least a portion of sample-containing fluid collected in the output well, and, optionally, a step of thermocycling the at least a portion of sample-containing fluid collected in the output well.

25. A microfluidic system for fluid processing, comprising: (A) a well component including a well; and (B) a channel component including (i) a body having a bottom surface attached to the well component and a top surface having a microchannel formed therein, (ii) an input tube projecting from the bottom surface of the body into the well, and (iii) a port, wherein the body and the input tube collectively define a passage extending upward from an open end of the input tube, through the input tube and the body, to the top surface, and wherein the system is configured to receive a sample-containing fluid in the well via the port from above the channel component and to retain the sample-containing fluid below a top end of the passage, with assistance from gravity, until a pressure differential is created that drives at least a portion of the sample-containing fluid out of the well via the passage and into the microchannel.

26. The system of paragraph 25, wherein the well is an input well, further comprising an output well disposed under the channel component, and wherein system is configured such that the pressure differential drives at least a portion of the sample-containing fluid from the input well to the output well.

27. The system of paragraph 26, wherein the passage is an input passage, wherein the channel component includes an output tube attached to the body and projecting from the bottom surface thereof into the output well, and wherein the body and the output tube collectively define an output passage through which the sample-containing fluid travels for collection in the output well.

28. The system of any of paragraphs 25 to 27, wherein the well is an input well, wherein the well component includes an output well, wherein the body has a channel network formed in the top surface, and wherein the channel network includes the microchannel and is configured to receive at least a portion of the sample-containing fluid from the input well via the passage and to generate an emulsion of sample-containing droplets disposed in a carrier fluid for collection in the output well.

29. The system of any of paragraphs 25 to 28, wherein the well component includes a carrier well to supply a carrier fluid to the channel network.

30. The system of any of paragraphs 25 to 29, wherein the channel component includes a carrier port configured to receive a carrier fluid for the channel network from above the channel component, such that the carrier fluid is introduced into the channel network from the carrier port without contacting the well component.

31. The system of any of paragraphs 25 to 30, wherein the body has a channel network formed in the top surface, and wherein the channel network is configured to receive at least a portion of the sample-containing fluid from the well via the passage and to generate sample-containing droplets disposed in a carrier fluid.

32. The system of any of paragraphs 25 to 31, wherein the well component includes a plurality of sample wells to hold a plurality of samples, and wherein the channel network includes a manifold to supply carrier fluid for generating sample-containing droplets from each of the plurality of samples.

33. The system of any of paragraphs 25 to 32, wherein the channel component includes a vacuum port configured to be connected to a vacuum source.

34. The system of any of paragraphs 25 to 33, further comprising a cover attached in a fluid-tight seal to the top surface of the body and forming a top wall of the microchannel.

35. The system of paragraph 34, wherein the body defines a vacuum port that is covered by the cover and configured to be connected to a vacuum source at least in part by piercing the cover.

36. The system of any of paragraphs 25 to 35, further comprising a device including the well component and the channel component, and even further comprising an instrument including the vacuum source and configured to pierce the cover and apply a vacuum to the device such that a plurality of emulsions are formed in the device and collected in different wells of the well component.

37. The system of paragraph 36, wherein the plurality of emulsions are formed in a same channel network of the device, and wherein the instrument is configured to supply a carrier fluid to the channel network such that the carrier fluid in introduced into the channel network before contacting the well component.

38. The system of any of paragraphs 25 to 37, wherein the body defines a carrier port that is configured to receive a carrier fluid through an opening in the cover.

39. The system of any of paragraphs 25 to 38, wherein the input tube and the body of the channel component are formed integrally with one another.

40. A system for fluid processing, comprising: (A) a well; and (B) a channel component including (i) a body including a bottom surface attached to the well, (ii) an input tube projecting into the well from the bottom surface of the body, (iii) a passage extending through the input tube and the body, and (iv) a microchannel, wherein the system is configured to receive a sample-containing fluid in the well such that the sample-containing fluid is in contact with a bottom end of the passage and is retained, with assistance from gravity, below a top end of the passage and out of contact with the microchannel until a pressure differential is created that drives at least a portion of the sample-containing fluid from the well via the passage and through the microchannel.

41. The system of paragraph 40, wherein the body defines a plane, and wherein the microchannel is parallel to the plane.

42. The system of paragraph 40 or paragraph 41, wherein the microchannel is formed in a top surface of the body.

43. The system of paragraph 40 or paragraph 41, wherein the channel component includes a cap attached to a top surface of the body, and wherein the microchannel is formed in a bottom surface of the cap.

44. The system of paragraph 43, wherein the cap is formed by a single sheet of material.

45. The system of paragraph 43, wherein the cap includes an upper sheet forming a top wall of the microchannel and a lower sheet forming lateral side walls of the microchannel, and wherein the body forms a bottom wall of the microchannel.

46. The system of any of paragraphs 40 to 45, wherein the well is an input well, further comprising an output well disposed under the channel component, and wherein system is configured such that the pressure differential drives at least a portion of the sample-containing fluid from the input well to the output well.

47. The system of paragraph 46, wherein the input well and the output well are formed integrally with one another and separately from the body and the input tube.

48. The system of paragraph 46 or paragraph 47, wherein the body and the input tube are molded as a single piece, and wherein the input well and the output well are molded as another single piece.

49. The system of any of paragraphs 46 to 48, wherein the channel component includes a channel network, and wherein the channel network is configured to receive at least a portion of the sample-containing fluid and to generate sample-containing droplets for collection in the output well.

50. The system of paragraph 49, wherein the channel network is formed in a top surface of the body.

51. The system of paragraph 49 or paragraph 50, further comprising a plurality of input wells and a plurality of output wells, wherein the channel component is configured to form a plurality of emulsions from at least one sample-containing fluid disposed in the plurality of input wells and to direct the plurality of emulsions to the plurality of output wells.

52. The system of paragraph 51, wherein each emulsion includes a same carrier fluid that forms a continuous phase of the emulsion, and wherein the channel network includes a manifold that supplies the same carrier fluid for each emulsion.

53. The system of any of paragraphs 46 to 52, further comprising a step of deforming a region of at least one channel of the channel component that provides communication between the input well and the output well such that fluid cannot pass through the least one channel.

54. The system of paragraph 53, wherein the step of deforming includes a step of applying pressure to the channel component over the region of the at least one channel.

55. The system of paragraph 53 or paragraph 54, when the step of deforming includes a step of applying heat to the channel component over the region of the at least one channel.

56. The system of any of paragraphs 53 to 55, when the step of deforming includes a step of melting the channel component at the region of the at least one channel.

57. The system of any of paragraphs 53 to 56, wherein the step of deforming includes a step of creating a longitudinal region of the at least one channel at which the channel is collapsed.

58. The system of any of paragraphs 53 to 57, when the step of deforming includes a step of deforming a region of each of two or more channels at the same time such that fluid cannot pass through any of the two or more channels.

59. The system of paragraph 58, wherein each of the two or more channels extend from a same output well.

60. The system of paragraph 59, wherein the step of deforming includes a step of deforming a region of each channel that extends from the output well such that the output well is fluidically isolated.

61. The system of any of paragraphs 53 to 60, wherein the step of deforming includes a step of fluidically isolating a plurality of output wells in parallel.

62. The system of any of paragraphs 53 to 61, wherein the step of deforming includes a step of deforming a separate region of the channel component for each output well.

63. The system of any of paragraphs 53 to 61, further comprising a step of thermally cycling fluid in the output well after the step of deforming.

64. The system of paragraph 63, wherein the step of thermally cycling fluid causes amplification of nucleic acid in the fluid.

65. The system of paragraph 63 or paragraph 64, wherein the step of thermally cycling fluid includes a step of thermally cycling a plurality of separate emulsions contained by output wells of the system.

66. The system of any of paragraphs 40 to 65, wherein the channel component includes a carrier port connected to the channel network and configured to receive a carrier fluid that enters the carrier port from above the channel component in response to the pressure differential.

66. The system of any of paragraphs 40 to 65, wherein the channel component includes a cover disposed on the top surface of the body, further comprising an instrument configured to pierce the cover and apply a vacuum or pressure to the channel component through the pierced cover to drive flow of the sample-containing fluid from the well and through the microchannel.

67. The system of any of paragraphs 40 to 66, wherein the body and the input tube are formed integrally with one another and separately from the well.

68. The system of any of paragraphs 40 to 67, wherein the channel component defines a sample port over the well and separate from the passage for introduction of the sample-containing fluid into the well.

69. The system of any of paragraphs 40 to 68, wherein the channel component includes a cover attached in a fluid-tight seal to the top surface of the body and providing a top wall for the microchannel.

70. The system of paragraph 69, wherein the channel component includes at least one port covered by the cover and configured to be accessed by piercing the cover.

71. The system of any of paragraphs 40 to 70, wherein the channel component includes a base including the body and the input tube and also includes a cover disposed on the base and at least partially covering each of a plurality of ports defined by the base and each fluidically connected to the microchannel.

72. A method of processing fluid, the method comprising: (A) dispensing a sample-containing fluid into a well of a well component via a port defined by a channel component, the channel component including (i) a body having a bottom surface attached to the well component and a top surface having a microchannel formed therein, and (ii) an input tube attached to the body and projecting from the bottom surface of the body to a lower inside region of the well, the channel component defining a passage that extends from an open bottom end of the input tube to a top surface of the body, wherein the sample-containing fluid is in contact with the open bottom end and is retained below a top end of the passage with assistance from gravity; and (B) creating a pressure differential that drives at least a portion of the sample-containing fluid out of the well via the passage and into the microchannel.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of processing fluid, the method comprising: selecting a microfluidic device including at least one well component, the at least one well component providing an input well and an output well, the microfluidic device also including a channel component attached directly to a top side of the at least one well component, the channel component including
   (a) a substantially planar body including a microchannel disposed substantially horizontally in operation,
   (b) an input tube projecting from the body and located in the input well, and
   (c) a sample port that communicates with the input well separately from the input tube;
introducing, with a fluid-transfer device, a sample-containing fluid into the input well through the sample port and into contact with a bottom end of the input tube;
operatively connecting at least one vacuum/pressure source to the microfluidic device; and
creating a pressure differential with the at least one vacuum/pressure source that drives at least a portion of the sample-containing fluid from the input well to the output well on a path defined by the channel component, wherein the path extends upward through the input tube, through the microchannel, and downward to the output well.

2. The method of claim 1, wherein a channel network including the microchannel is formed in a top surface of the body, further comprising a step of generating an emulsion of sample-containing droplets in the channel network.

3. The method of claim 2, further comprising a step of collecting at least a portion of the emulsion in the output well.

4. The method of claim 3, wherein the step of introducing includes a step of introducing at least one sample-containing fluid into each of a plurality of input wells provided by the at least one well component, and wherein the step of collecting includes a step of collecting a plurality of emulsions in a plurality of output wells provided by the at least one well component.

5. The method of claim 1, wherein the channel component includes a cover disposed on a top surface of the body and forming a top wall of the microchannel, and wherein the step of creating a pressure differential includes a step of applying a vacuum or positive pressure to the channel component at an opening defined by the cover.

6. The method of claim 4, wherein each emulsion of the plurality of emulsions is formed in the same channel network, and wherein each emulsion of the plurality of emulsions is formed at a different region of the channel network than each other emulsion of the plurality of emulsions.

7. The method of claim 4, wherein droplets of each emulsion of the plurality of emulsions are disposed in a carrier fluid that forms a continuous phase of the emulsion, further comprising a step of supplying at least a portion of the carrier fluid to the channel network from a carrier port of the channel component that receives the carrier fluid from a position over the carrier port in response to the pressure differential.

8. The method of claim 1, wherein the step of creating a pressure differential includes a step of piercing a cover disposed on the top surface of the body to create an opening in the cover, and a step of applying a vacuum or positive pressure to the channel component at the opening.

9. The method of claim 1, further comprising a step of collecting at least a portion of the sample-containing fluid in the output well, and a step of deforming one or more channels that communicate with the output well to block fluid flow through the one or more channels and fluidically isolate the at least a portion of sample-containing fluid collected in the output well.

10. The method of claim 9, further comprising a step of thermocycling the at least a portion of sample-containing fluid while such portion of sample-containing fluid is contained by the output well.

11. A method of processing fluid, the method comprising:
  selecting a microfluidic device including at least one well component, the at least one well component providing an input well and an output well, the microfluidic device also including a channel component attached directly to a top side of the at least one well component, the channel component including
    (a) a body having a top surface, wherein a plurality of microchannels are formed in the top surface, and wherein the plurality of microchannels meet one another at a channel intersection,
    (b) a cover bonded to the top surface of the body and forming a top wall of each of the plurality of microchannels,
    (c) an input tube projecting from a bottom surface of the body and located in the input well, and
    (d) a sample port that communicates with the input well separately from the input tube;
  introducing, with a fluid-transfer device, a sample-containing fluid into the input well through the sample port and into contact with a bottom end of the input tube;
  operatively connecting at least one vacuum/pressure source to the microfluidic device; and
  creating a pressure differential with the at least one vacuum/pressure source that drives at least a portion of the sample-containing fluid from the input well to the output well on a path defined by the channel component, wherein the path extends upward through the input tube, through the channel intersection, and downward to the output well.

12. The method of claim 11, further comprising a step of forming sample-containing droplets at the channel intersection in response to the step of creating a pressure differential.

13. The method of claim 12, further comprising a step of collecting an emulsion including the sample-containing droplets in the output well.

14. The method of claim 13, further comprising a step of connecting the channel component to a source of carrier fluid, wherein the step of creating a pressure differential includes a step of driving carrier fluid from the source to the channel intersection, and wherein the emulsion includes the carrier fluid as a continuous phase.

15. The method of claim 12, wherein the channel component includes a plurality of channel intersections, and wherein the step of creating a pressure differential includes a step of forming a respective set of sample-containing droplets at each of the channel intersections.

16. The method of claim 15, the at least one well component providing a plurality of output wells, further comprising a step of collecting each respective set of sample-containing droplets in a different one of the output wells.

17. The method of claim 11, wherein the step of creating a pressure differential includes a step of applying a vacuum to the output well.

* * * * *